(12) United States Patent
Chiu et al.

(10) Patent No.: US 10,768,180 B2
(45) Date of Patent: Sep. 8, 2020

(54) POLYELECTROLYTE-COATED POLYMER DOTS AND RELATED METHODS

(71) Applicant: University of Washington through its Center for Commercialization, Seattle, WA (US)

(72) Inventors: Daniel T. Chiu, Seattle, WA (US); Yuhui Jin, Painted Post, NY (US); Fangmao Ye, Seattle, WA (US); Changfeng Wu, Changchun (CN); Yang-Hsiang Chan, Seattle, WA (US)

(73) Assignee: UNIVERSITY OF WASHINGTON THROUGH ITS CENTER FOR COMMERCIALIZATION, Seattle, WA (US)

( * ) Notice: Subject to any disclaimer, the term of this patent is extended or adjusted under 35 U.S.C. 154(b) by 0 days.

(21) Appl. No.: 16/041,569

(22) Filed: Jul. 20, 2018

(65) Prior Publication Data

US 2019/0004056 A1 Jan. 3, 2019

Related U.S. Application Data

(63) Continuation of application No. 14/373,835, filed as application No. PCT/US2013/024300 on Feb. 1, 2013, now Pat. No. 10,067,139.

(60) Provisional application No. 61/594,564, filed on Feb. 3, 2012.

(51) Int. Cl.
| | |
|---|---|
| *G01N 33/58* | (2006.01) |
| *H01L 51/00* | (2006.01) |
| *B82Y 40/00* | (2011.01) |
| *A61K 49/00* | (2006.01) |
| *H01L 51/50* | (2006.01) |
| *B82Y 15/00* | (2011.01) |
| *B82Y 5/00* | (2011.01) |

(52) U.S. Cl.
CPC ....... *G01N 33/588* (2013.01); *A61K 49/0065* (2013.01); *B82Y 40/00* (2013.01); *H01L 51/0036* (2013.01); *H01L 51/0039* (2013.01); *H01L 51/0043* (2013.01); *B82Y 5/00* (2013.01); *B82Y 15/00* (2013.01); *H01L 51/5012* (2013.01)

(58) Field of Classification Search
None
See application file for complete search history.

(56) References Cited

U.S. PATENT DOCUMENTS

| | | |
|---|---|---|
| 4,774,339 A | 9/1988 | Haugland et al. |
| 4,946,778 A | 8/1990 | Ladner et al. |
| 5,723,218 A | 3/1998 | Haugland et al. |
| 6,417,402 B1 | 7/2002 | Das et al. |
| 7,432,298 B2 | 10/2008 | Lam et al. |
| 7,462,325 B2 | 12/2008 | Hancock et al. |
| 7,521,232 B2 | 4/2009 | Moon |
| 7,985,426 B1 | 7/2011 | Sung et al. |
| 8,367,042 B2 | 2/2013 | Kim et al. |
| 9,382,473 B2 | 7/2016 | Chiu et al. |
| 9,797,840 B2 | 10/2017 | Chiu et al. |
| 9,810,693 B2 | 11/2017 | Chiu et al. |
| 9,849,197 B2 | 12/2017 | Saji et al. |
| 10,067,139 B2 | 9/2018 | Chiu et al. |
| 10,150,841 B2 | 12/2018 | Chiu et al. |
| 10,191,060 B2 | 1/2019 | Chiu et al. |
| 2002/0045045 A1 | 4/2002 | Adams et al. |
| 2004/0018379 A1 | 1/2004 | Kinlen |
| 2004/0131886 A1 | 7/2004 | Marrocco et al. |
| 2005/0019265 A1 | 1/2005 | Hammer et al. |
| 2005/0171289 A1 | 8/2005 | Kataoka et al. |
| 2005/0255044 A1 | 11/2005 | Lomnes et al. |
| 2006/0127929 A1 | 6/2006 | Swager et al. |
| 2007/0031490 A1 | 2/2007 | Loebenberg et al. |
| 2007/0224345 A1 | 9/2007 | Metz et al. |
| 2008/0081192 A1 | 4/2008 | Goh et al. |
| 2008/0085566 A1 | 4/2008 | Swager et al. |
| 2008/0178763 A1 | 7/2008 | Schwartz et al. |
| 2008/0199700 A1 | 8/2008 | Anderson et al. |
| 2008/0242806 A1 | 10/2008 | Chen et al. |
| 2009/0075295 A1 | 3/2009 | Lindsey |
| 2009/0130665 A1 | 5/2009 | Sleiman et al. |
| 2009/0220434 A1 | 9/2009 | Sharma |
| 2010/0016472 A1 | 1/2010 | Wang et al. |
| 2010/0098902 A1 | 4/2010 | Kotov et al. |
| 2010/0290999 A1 | 11/2010 | Kim et al. |
| 2011/0159605 A1 | 6/2011 | Whitten et al. |
| 2011/0278503 A1 | 11/2011 | Janczewski et al. |
| 2011/0278536 A1 | 11/2011 | Walker et al. |
| 2012/0015190 A1 | 1/2012 | Goh et al. |
| 2012/0175571 A1 | 7/2012 | Sarkar |

(Continued)

FOREIGN PATENT DOCUMENTS

| | | |
|---|---|---|
| CN | 1541136 A | 10/2004 |
| CN | 101302353 A | 11/2008 |

(Continued)

OTHER PUBLICATIONS

Abbel, et al. Multicolour self-assembled particles of fluorene-based bolaamphiphiles. Chem Commun (Camb). Apr. 7, 2009;(13):1697-9. doi: 10.1039/b822943k. Epub Feb. 17, 2009.

(Continued)

*Primary Examiner* — James W Rogers
(74) *Attorney, Agent, or Firm* — Christensen O'Connor Johnson Kindness PLLC

(57) ABSTRACT

Polymer nanoparticles and related methods are provided. The polymer particles can include polymer dots having a coating including a polyelectrolyte polymer. Methods of making and using the polymer nanoparticles are also provided.

21 Claims, 6 Drawing Sheets

(56) References Cited

U.S. PATENT DOCUMENTS

| | | |
|---|---|---|
| 2012/0282632 A1 | 11/2012 | Chiu et al. |
| 2013/0234067 A1 | 9/2013 | Chiu et al. |
| 2013/0234068 A1 | 9/2013 | Chiu et al. |
| 2013/0266957 A1 | 10/2013 | Chiu et al. |
| 2014/0302516 A1 | 10/2014 | Chiu et al. |
| 2014/0350183 A1 | 11/2014 | Chiu et al. |
| 2016/0018395 A1 | 1/2016 | Chiu et al. |
| 2016/0161475 A1 | 6/2016 | Chiu et al. |
| 2016/0341737 A1 | 11/2016 | Chiu et al. |

FOREIGN PATENT DOCUMENTS

| | | |
|---|---|---|
| CN | 102791827 A | 11/2012 |
| JP | 2006525527 A | 11/2006 |
| JP | 2013168424 A | 8/2013 |
| WO | WO-2007027159 A1 | 3/2007 |
| WO | WO-2007095506 A1 | 8/2007 |
| WO | WO-2008063378 A2 | 5/2008 |
| WO | WO-2009051560 A1 | 4/2009 |
| WO | WO-2009107859 A2 | 9/2009 |
| WO | WO-2010006753 A2 | 1/2010 |
| WO | WO-2010075512 A1 | 7/2010 |
| WO | WO-2010075514 A1 | 7/2010 |
| WO | WO-2010099273 A1 | 9/2010 |
| WO | WO-2011057295 A2 | 5/2011 |
| WO | WO-2012054525 A2 | 4/2012 |
| WO | WO-2012118136 A1 | 9/2012 |
| WO | WO-2013101902 A2 | 7/2013 |
| WO | WO-2013116614 A1 | 8/2013 |
| WO | WO-2014153051 A1 | 9/2014 |

OTHER PUBLICATIONS

Achari, et al. 1.67—A X-ray structure of the B2 immunoglobulin-binding domain of streptococcal protein G and comparison to the NMR structure of the B1 domain. Biochemistry. Nov. 3, 1992;31(43):10449-57.

Agard, et al. A comparative study of bioorthogonal reactions with azides. ACS Chem Biol. Nov. 21, 2006;1(10):644-8.

Akerstrom, et al. A physicochemical study of protein G, a molecule with unique immunoglobulin G-binding properties. J Biol Chem. Aug. 5, 1986;261(22):10240-7.

Alivistatos, et al. Quantum dots as cellular probes. Annu Rev Biomed Eng. 2005;7:55-76.

Ausborn, et al. The protective effect of free and membrane-bound cryoprotectants during freezing and freeze-drying of liposomes. Journal of Controlled Release. 1994; 30:105-116.

Australian Examination Report dated Jun. 13, 2018 for AU Application No. AU2017204805.

Baier, et al. Fluorescent conjugated polymer nanoparticles by polymerization in miniemulsion. J Am Chem Soc. Oct. 14, 2009;131(40):14267-73. doi: 10.1021/ja905077c.

Berlier, et al. Quantitative comparison of long-wavelength Alexa Fluor dyes to Cy dyes: fluorescence of the dyes and their bioconjugates. J Histochem Cytochem. Dec. 2003;51(12):1699-712.

Bernardin, et al. Copper-free click chemistry for highly luminescent quantum dot conjugates: application to in vivo metabolic imaging. Bioconjug Chem. Apr. 21, 2010;21(4):583-8. doi: 10.1021/bc900564w.

Best. Click chemistry and bioorthogonal reactions: unprecedented selectivity in the labeling of biological molecules. Biochemistry. Jul. 21, 2009;48(28):6571-84. doi: 10.1021/bi9007726.

Bird, et al. Single-chain antigen-binding proteins. Science. Oct. 21, 1988;242(4877):423-6.

Breidenbach, et al. Targeted metabolic labeling of yeast N-glycans with unnatural sugars. Proc Natl Acad Sci U S A. Mar. 2, 2010;107(9):3988-93. doi: 10.1073/pnas.0911247107. Epub Feb. 8, 2010.

Bruchez, et al. Semiconductor nanocrystals as fluorescent biological labels. Science. Sep. 25, 1998;281(5385):2013-6.

CA2814790 Office Action dated May 28, 2018.

Caruso. Nanoengineering of Particle Surfaces. Adv. Mater. 2001; 13:11-22.

Chalfie, et al. Green fluorescent protein as a marker for gene expression. Science. Feb. 11, 1994;263(5148):802-5.

Chan, et al. Copper(II) and iron(II) ion sensing with semiconducting polymer dots. Chem Commun (Camb). Mar. 14, 2011;47(10):2820-2. doi: 10.1039/c0cc04929h. Epub Jan. 14, 2011.

Chan, et al. Development of ultrabright semiconducting polymer dots for ratiometric pH sensing. Anal Chem. Feb. 15, 2011;83(4):1448-55. doi: 10.1021/ac103140x. Epub Jan. 18, 2011.

Chan, et al. Hybrid semiconducting polymer dot-quantum dot with narrow-band emission, near-infrared fluorescence, and high brightness. J Am Chem Soc. May 2, 2012;134(17):7309-12. doi: 10.1021/ja3022973. Epub Apr. 23, 2012.

Chan, et al. Quantum dot bioconjugates for ultrasensitive nonisotopic detection. Science. Sep. 25, 1998;281(5385):2016-8.

Chan, et al. Ultrasensitive copper(II) detection using plasmon-enhanced and photo-brightened luminescence of CdSe quantum dots. Anal Chem. May 1, 2010;82(9):3671-8. doi: 10.1021/ac902985p.

Chen, et al. Highly sensitive biological and chemical sensors based on reversible fluorescence quenching in a conjugated polymer. Proc Natl Acad Sci U S A. Oct. 26, 1999;96(22):12287-92.

Choi, et al. Design considerations for tumour-targeted nanoparticles. Nat Nanotechnol. Jan. 2010;5(1):42-7. doi: 10.1038/nnano.2009.314. Epub Nov. 1, 2009.

Choi, et al. Renal clearance of quantum dots. Nat Biotechnol. Oct. 2007;25(10):1165-70. Epub Sep. 23, 2007.

Clafton, et al. Chemical defects in the highly fluorescent conjugated polymer dots. Langmuir. Dec. 7, 2010;26(23):17785-9. doi: 10.1021/la103063p. Epub Nov. 11, 2010.

CN 201280070923.3 Fourth Office Action dated Apr. 23, 2018 (w/ English translation).

"CN 201480028351.1 Third Office Action dated Mar. 28, 2018 (w/ English translation)".

Collini, et al. Coherent intrachain energy migration in a conjugated polymer at room temperature. Science. Jan. 16, 2009;323(5912):369-73. doi: 10.1126/science.1164016.

"Corrected Notice of Allowability dated Dec. 1, 2017 for U.S. Appl. No. 13/508,981".

Derfus, et al. Probing the Cytotoxicity of Semiconductor Quantum Dots. Nano Letters. 2004;4(1):11-18.

Dieterich, et al. Selective identification of newly synthesized proteins in mammalian cells using bioorthogonal noncanonical amino acid tagging (BONCAT). Proc Natl Acad Sci U S A. Jun. 20, 2006;103(25):9482-7. Epub Jun. 12, 2006.

Dube, et al. Probing mucin-type O-linked glycosylation in living animals. Proc Natl Acad Sci U S A. Mar. 28, 2006;103(13):4819-24. Epub Mar. 20, 2006.

European search report and opinion dated Mar. 19, 2014 for EP Application No. 11835019.8.

European search report and opinion dated Aug. 12, 2015 for EP Application No. 15175146.8.

European search report and opinion dated Sep. 18, 2013 for EP Application No. 10829306.9.

European search report and opinion dated Oct. 8, 2015 for EP Application No. 13743132.6.

Fan, et al. Beyond superquenching: hyper-efficient energy transfer from conjugated polymers to gold nanoparticles. Proc Natl Acad Sci U S A. May 27, 2003;100(11):6297-301. Epub May 15, 2003.

Fernandez-Suarez, et al. Fluorescent probes for super-resolution imaging in living cells. Nat Rev Mol Cell Biol. Dec. 2008;9(12):929-43. doi: 10.1038/nrm2531. Epub Nov. 12, 2008.

Fernando, et al. Mechanism of cellular uptake of highly fluorescent conjugated polymer nanoparticles. Biomacromolecules. Oct. 11, 2010;11(10):2675-82. doi: 10.1021/bm1007103.

Friend, et al. Electroluminescence in conjugated polymers. Nature. 1999; 397:121-128.

Giepmans, et al. The fluorescent toolbox for assessing protein location and function. Science. Apr. 14, 2006;312(5771):217-24.

Green. Avidin and streptavidin. Methods Enzymol. Wilchek and Bayer. New York, Academic Press, Inc. 1990;184:51-67.

(56) References Cited

OTHER PUBLICATIONS

Greenham et al., Efficient light-emitting diodes based on polymers with high electron affinities, Nature, vol. 365:628-630, published Oct. 14, 1993, print retrieved on Oct. 10, 2016.
Gunes, et al. Conjugated polymer-based organic solar cells. Chem Rev. Apr. 2007;107(4):1324-38.
Han, et al. Development of a bioorthogonal and highly efficient conjugation method for quantum dots using tetrazine-norbornene cycloaddition. J Am Chem Soc. Jun. 16, 2010;132(23):7838-9. doi: 10.1021/ja101677r.
Hashim, et al. Luminescent quantum-dot-sized conjugated polymer nanoparticles—nanoparticle formation in miniemulsion system. Journal of Materials Chemistry. 2011; 21: 1797-1803.
Hermanson. Bioconjugate techniques, Academic Press, San Diego, 1996; Ch 13, 570-591.
Hou, et al. Novel red-emitting fluorene-based copolymers. Journal of Materials Chemistry. 2002; 12:2887-2892.
Hou, et al. Synthesis and electroluminescent properties of high-efficiency saturated red emitter based on copolymers from fluorene and 4,7-di(4-hexylthien-2-yl)-2,1,3-benzothiadiazole, Macromolecules. 2004; 37:6299-6305.
Howarth, et al. Monovalent, reduced-size quantum dots for imaging receptors on living cells. Nat Methods. May 2008;5(5):397-9. doi: 10.1038/nmeth.1206. Epub Apr. 20, 2008.
Howes, et al. Colloidal and optical stability of PEG-capped and phospholipid-encapsulated semiconducting polymer nanospheres in different aqueous media. Photochem Photobiol Sci. Aug. 2010;9(8):1159-66. doi: 10.1039/c0pp00106f. Epub Jun. 29, 2010.
Howes, et al. Magnetic conjugated polymer nanoparticles as bimodal imaging agents. J Am Chem Soc. Jul. 21, 2010;132(28):9833-42. doi: 10.1021/ja1031634.
Howes, et al. Phospholipid encapsulated semiconducting polymer nanoparticles: their use in cell imaging and protein attachment. J Am Chem Soc. Mar. 24, 2010;132(11):3989-96. doi: 10.1021/ja1002179.
Howes, et al. Synthesis, characterisation and intracellular imaging of PEG capped BEHP-PPV nanospheres. Chem Commun (Camb). May 14, 2009;(18):2490-2. doi: 10.1039/b903405f. Epub Apr. 2, 2009.
Huyal, et al., White emitting polyfluorene functionalized with azide hybridized on near-UV light emitting diode for high color rendering index, Optics Express , Jan. 21, 2008, 16(2):1115-24.
International preliminary report on patentability dated Apr. 23, 2013 for PCT/US2011/056768.
International search report and written opinion dated Mar. 27, 2013 for PCT/US2012/071767.
International search report and written opinion dated Apr. 9, 2013 for PCT/US2013/024300.
International search report and written opinion dated Jun. 26, 2012 for PCT/US2011/056768.
International search report and written opinion dated Jul. 28, 2011 for PCT/US2010/056079.
International search report and written opinion dated Aug. 22, 2014 for PCT/US2014/028846.
"Jin, et al., Generation of functionalized and robust semiconducting polymer dots with polyelectrolytes, Chem Commun (Camb). Mar. 28, 2012;48(26): doi: 10.1039/c2cc17703j.".
Jin, et al. Near-infrared fluorescent dye-doped semiconducting polymer dots. ACS Nano. Feb. 22, 2011;5(2):1468-75. doi: 10.1021/nn103304m. Epub Jan. 31, 2011.
Jin, et al. Silica Nanoparticles with Continuously Tunable Sizes: Synthesis and Size Effects on Cellular Imaging. Chem. Mater. 2008, 20:4411-4419.
Johnston, et al. Layer-by-layer engineered capsules and their applications. Curr. Opin. Colloid Interface Sci. 2006; 11:203-209.
"JP 2016-235598 Office Action dated Mar. 28, 2018 (w/ English translation)".
Kaeser, et al. Fluorescent nanoparticles based on self-assembled pi-conjugated systems. Adv Mater. Jul. 27, 2010;22(28):2985-97. doi: 10.1002/adma.201000427.
Kietzke, et al. Novel approaches to polymer blends based on polymer nanoparticles. Nat Mater. Jun. 2003;2(6):408-12.
Kim, et al. Conjugated polymer nanoparticles for biomedical in vivo imaging. Chem Commun (Camb). Mar. 14, 2010;46(10):1617-9. doi: 10.1039/b923309a. Epub Jan. 12, 2010.
Kolb, et al. Click Chemistry: Diverse Chemical Function from a Few Good Reactions. w Chem Int Ed Engl. Jun. 1, 2001;40(11):2004-2021.
Kolb, et al. The growing impact of click chemistry on drug discovery. Drug Discov Today. Dec. 15, 2003;8(24):1128-37.
Kumar, et al. Photon antibunching from oriented semiconducting polymer nanostructures. J Am Chem Soc. Mar. 24, 2004;126(11):3376-7.
Laughlin, et al. Imaging the glycome. Proc Natl Acad Sci U S A. Jan. 6, 2009;106(1):12-7. doi: 10.1073/pnas.0811481106. Epub Dec. 22, 2008.
Lee, et al. Recent advances in fluorescent and colorimetric conjugated polymer-based biosensors. Analyst. Sep. 2010;135(9):2179-89. doi: 10.1039/c0an00239a. Epub Jun. 11, 2010.
Li, et al. Polymer encapsulated conjugated polymer nanoparticles for fluorescence bioimaging. Journal of Materials Chemistry 2012; 22:1257-1264.
McCafferty, et al. Phage antibodies: filamentous phage displaying antibody variable domains. Nature. Dec. 6, 1990;348(6301):552-4.
Meng, et al. Color tuning of polyfluorene emission with BODIPY monomers, Macromolecules 2009, 42:1995-2001.
Michalet, et al. Quantum dots for live cells, in vivo imaging, and diagnostics. Science. Jan. 28, 2005;307(5709):538-44.
Moon, et al. Conjugated polymer nanoparticles for small interfering RNA delivery. Chem Commun (Camb). Aug. 7, 2011;47(29):8370-2. doi: 10.1039/c1cc10991j. Epub Jun. 22, 2011.
Moon, et al. Live-cell-permeable poly(p-phenylene ethynylene). Angew Chem Int Ed Engl. 2007;46(43):8223-5.
Moses, et al. The growing applications of click chemistry. Chem Soc Rev. Aug. 2007;36(8):1249-62. Epub May 3, 2007.
Nirmal, et al. Fluorescence intermittency in single cadmium selenide nanocrystals. Nature. 1996; 383:802-804. doi:10.1038/383802a0.
Notice of allowance dated Jun. 27, 2018 for U.S. Appl. No. 14/366,863.
Notice of allowance dated Jul. 23, 2018 for U.S. Appl. No. 14/366,863.
Notice of allowance dated Aug. 8, 2018 for U.S. Appl. No. 14/373,835.
Notice of allowance dated Sep. 6, 2018 for U.S. Appl. No. 13/508,981.
"Notice of Allowance dated Oct. 19, 2017 for U.S. Appl. No. 13/508,981".
Office action dated Feb. 2, 2016 for CN Application No. 201180068242.
Office action dated Feb. 4, 2015 for CN Application No. 201180068242.
Office action dated Mar. 8, 2017 for AU Application No. 2015204342.
Office action dated Mar. 29, 2016 for JP Application No. 2012-538915.
Office action dated Mar. 30, 2017 for U.S. Appl. No. 14/373,835.
Office action dated Apr. 5, 2017 for EP Application No. 15175146.8.
Office action dated Apr. 28, 2014 for AU Application No. 2011317142.
Office action dated May 16, 2016 for U.S. Appl. No. 14/373,835.
Office action dated May 20, 2016 for EP Application No. 10829306.9.
Office action dated May 30, 2014 for CN Application No. 201180068242.
"Office action dated Jun. 23, 2017 for CN Application No. 201480028351.1".
Office action dated Jun. 29, 2018 for U.S. Appl. No. 14/774,971.
"Office action dated Jul. 26, 2017 for CN Application No. 201280070923.3".
Office action dated Aug. 4, 2015 for CN Application No. 201180068242.
"Office action dated Sep. 21, 2017 for EP Application No. 15175146.8".
"Office action dated Sep. 22, 2017 for EP Application No. 11835019.8".
Office action dated Sep. 29, 2016 for CN Application No. 201180060824.2.
"Office Action dated Oct. 10, 2017 for U.S. Appl. No. 14/366,863".

(56) References Cited

OTHER PUBLICATIONS

Office action dated Oct. 20, 2016 for U.S. Appl. No. 13/687,813.
"Office Action dated Nov. 24, 2017 for CN Patent Application No. 201180060824.2".
"Office Action dated Nov. 30, 2017 for U.S. Appl. No. 14/373,835".
Office action dated Dec. 3, 2015 for JP Application No. 2013-535014.
Office action dated Dec. 29, 2016 for U.S. Appl. No. 13/865,942.
"Office Action dated Jan. 26, 2018 for EP Application No. 12861954.1".
Office action dated Jan. 30, 2017 for AU Application No. 2012362466.
Office action dated Feb. 22, 2017 for U.S. Appl. No. 13/508,981.
Office action dated Mar. 1, 2017 for U.S. Appl. No. 14/366,863.
Office action dated Sep. 13, 2016 for U.S. Appl. No. 14/373,835.
Palacios, et al. Charging and discharging of single conjugated-polymer nanoparticles. Nat Mater. Sep. 2007;6(9):680-5. Epub Jul. 22, 2007.
Park, et al., White-Emitting Conjugated Polymer Nanoparticles with Cross-Linked Shell for Mechanical Stability and Controllable photometric Properties in Color-Conversion LED Applications, ACS Nano, 2011, 5(4):2483-92.
Pecher, et al. Nanoparticles of conjugated polymers. Chem Rev. Oct. 13, 2010;110(10):6260-79. doi: 10.1021/cr100132y.
Pepperkok, et al. High-throughput fluorescence microscopy for systems biology. Nat Rev Mol Cell Biol. Sep. 2006;7(9):690-6. Epub Jul. 19, 2006.
Poon, et al. Controlling in vivo stability and biodistribution in electrostatically assembled nanoparticles for systemic delivery. Nano Lett. May 11, 2011;11(5):2096-103. doi: 10.1021/nl200636r. Epub Apr. 27, 2011.
Poon, et al. Layer-by-layer nanoparticles with a pH-sheddable layer for in vivo targeting of tumor hypoxia. ACS Nano. Jun. 28, 2011;5(6):4284-92. doi: 10.1021/nn200876f. Epub Apr. 29, 2011.
Pras, et al. Photoluminescence of 2,7-poly(9,9-dialkylfluorene-co-fluorenone) nanoparticles: effect of particle size and inert polymer addition. Langmuir. Sep. 21, 2010;26(18):14437-42. doi: 10.1021/la1011742.
Prescher, et al. Chemical remodelling of cell surfaces in living animals. Nature. Aug. 19, 2004;430(7002):873-7.
Prescher, et al. Chemistry in living systems. Nat Chem Biol. Jun. 2005;1(1):13-21.
Pu, et al. Fluorescent conjugated polyelectroltyes for bioimaging. Advanced Functional Materials. 2011; 21:3408-3423.
Pu, et al. Fluorescent single-molecular core-shell nanospheres of hyperbranched conjugated polyelectrolyte for live-cell imaging. Chem. Mater. 2009;21:3816-3822.
Que, et al. Metals in neurobiology: probing their chemistry and biology with molecular imaging. Chem Rev. May 2008;108(5):1517-49. doi: 10.1021/cr078203u. Epub Apr. 22, 2008.
Rahim, et al. Conjugated Polymer Nanoparticles for Two-Photon Imaging of Endothelial Cells in a Tissue Model. Adv. Mater. 2009; 21(34):3492-3496.
Resch-Genger, et al. Quantum dots versus organic dyes as fluorescent labels. Nat Methods. Sep. 2008;5(9):763-75. doi: 10.1038/nmeth.1248.
Sadtler, et al. Selective facet reactivity during cation exchange in cadmium sulfide nanorods. J Am Chem Soc. Apr. 15, 2009;131(14):5285-93. doi: 10.1021/ja809854q.
Sigma Aldrich. Product Information Triton X-1 00. Apr. 21, 1999. Retrieved at http://www.sigmaaldrich.com/content!dam/sigmaaldrich/docs/Sigma/Product_Information_Sheet/1/t8532pis.pdf on Mar. 14, 2014.
Sletten, et al. Bioorthogonal chemistry: fishing for selectivity in a sea of functionality. Angew Chem Int Ed Engl. 2009;48(38):6974-98. doi: 10.1002/anie.200900942.
Smith, et al. Investigating lyophilization of lipid nanocapsules with fluorescence correlation spectroscopy. Investigating lyophilization of lipid nanocapsules with fluorescence correlation spectroscopy.

Speers, et al. Activity-based protein profiling in vivo using a copper(i)-catalyzed azide-alkyne [3+2] cycloaddition. J Am Chem Soc. Apr. 23, 2003;125(16):4686-7.
Szymanski, et al. Single molecule nanoparticles of the conjugated polymer MEH-PPV, preparation and characterization by near-field scanning optical microscopy. J Phys Chem B. May 12, 2005;109(18):8543-6.
Thivierge, et al. Brilliant BODIPY-fluorene Copolymers With Dispersed Absorption and Emission Maxima. Macromolecules. May 24, 2011;44(10):4012-4015.
Thomas, et al. Chemical sensors based on amplifying fluorescent conjugated polymers. Chem Rev. Apr. 2007;107(4):1339-86. Epub Mar. 27, 2007.
Tian, et al. Amplified energy transfer in conjugated polymer nanoparticle tags and sensors. Nanoscale. Oct. 2010;2(10):1999-2011. doi: 10.1039/c0nr00322k. Epub Aug. 10, 2010.
Tsien. The green fluorescent protein. Annu Rev Biochem. 1998;67:509-44.
Tuncel, et al. Conjugated polymer nanoparticles. Nanoscale. Apr. 2010;2(4):484-94. doi: 10.1039/b9nr00374f. Epub Mar. 6, 2010.
"U.S. Appl. No. 14/373,835 Notice of Allowance dated Apr. 24, 2018".
"U.S. Appl. No. 14/774,971 Office Action dated Feb. 16, 2018".
Veiseh, et al. Specific targeting of brain tumors with an optical/magnetic resonance imaging nanoprobe across the blood-brain barrier. Cancer Res. Aug. 1, 2009;69(15):6200-7. doi: 10.1158/0008-5472.CAN-09-1157. Epub Jul. 28, 2009.
Wang, et al. Bioconjugation by copper(I)-catalyzed azide-alkyne [3+2] cycloaddition. J Am Chem Soc. Mar. 19, 2003;125(11):3192-3.
Wang, et al. Non-blinking semiconductor nanocrystals. Nature. Jun. 4, 2009;459(7247):686-9. doi: 10.1038/nature08072.
Wang, et al. Watching silica nanoparticles glow in the biological world. Anal. Chem. 2006;78(3):646-654.
Wu, et al. Bioconjugation of ultrabright semiconducting polymer dots for specific cellular targeting. J Am Chem Soc. Nov. 3, 2010;132(43):15410-7. doi: 10.1021/ja107196s.
Wu, et al. Conjugated polymer dots for multiphoton fluorescence imaging. J Am Chem Soc. Oct. 31, 2007;129(43):12904-5. Epub Oct. 6, 2007.
Wu, et al. Corrigendum: Immunofluorescent labeling of cancer marker Her2 and other cellular targets with semiconductor quantum dots. Nat Biotechnol. Jan. 2003;21(1):41-6. Epub Dec. 2, 2002.
Wu, et al. Design of highly emissive polymer dot bioconjugates for in vivo tumor targeting. Angew Chem Int Ed Engl. Apr. 4, 2011;50(15):3430-4. doi: 10.1002/anie.201007461. Epub Mar. 4, 2011.
Wu, et al. Energy Transfer in a Nanoscale Multichromophoric System: Fluorescent Dye-Doped Conjugated Polymer Nanoparticles. Phys Chem C Nanomater Interfaces. Feb. 14, 2008;112(6):1772-1781.
Wu, et al. Energy transfer mediated fluorescence from blended conjugated polymer nanoparticles. J Phys Chem B. Jul. 27, 2006;110(29):14148-54.
Wu, et al. Highly fluorescent semiconducting polymer dots for biology and medicine. Angew Chem Int Ed Engl. Mar. 11, 2013;52(11):3086-109. doi: 10.1002/anie.201205133. Epub Jan. 10, 2013.
Wu, et al. Immunofluorescent labeling of cancer marker Her2 and other cellular targets with semiconductor quantum dots. Nat Biotechnol. Jan. 2003;21(1):41-6. Epub Dec. 2, 2002.
Wu, et al. Multicolor conjugated polymer dots for biological fluorescence imaging. ACS Nano. Nov. 25, 2008;2(11):2415-23. doi: 10.1021/nn800590n.
Wu, et al. Preparation and encapsulation of highly fluorescent conjugated polymer nanoparticles. Langmuir. Mar. 28, 2006;22(7):2956-60.
Wu, et al. Ratiometric single-nanoparticle oxygen sensors for biological imaging. Angew Chem Int Ed Engl. 2009;48(15):2741-5. doi: 10.1002/anie.200805894.
Wu, et al. Swelling-controlled polymer phase and fluorescence properties of polyfluorene nanoparticles. Langmuir. Jun. 3, 2008;24(11):5855-61. doi: 10.1021/la8000762. Epub May 7, 2008.

(56) References Cited

OTHER PUBLICATIONS

Wu, et al. Ultrabright and bioorthogonal labeling of cellular targets using semiconducting polymer dots and click cAngew Chem Int Ed Engl. Dec. 3, 2010;49(49):9436-40. doi: 10.1002/anie.201004260. hemistry.
Wu. Fluorescent conjugated polymer dots for single molecule imaging and sensing application a Dissertation presented to the Graduate School of Clemson University. Dec. 1, 2008. pp. 1-182. http://etd.lib.clemson.edu/documents/1239895063/Wu_clemson_005D_10023.pdf.
Xie, et al. Luminescent CdSe—ZnSe quantum dots as selective Cu2+ probe. Spectrochimica Acta Part A. 2004; 60:2527-2530.
Xing, et al. Bioconjugated quantum dots for multiplexed and quantitative immunohistochemistry. Nat Protoc. 2007;2(5):1152-65.
Yang, et al. Deep-red electroluminescent polymers: Synthesis and characterization of new low-band-gap conjugated copolymers for light-emitting diodes and photovoltaic devices. Macromolecules 2005; 38:244-253.
Yao, et al. Blinking and nonradiant dark fraction of water-soluble quantum dots in aqueous solution. Proc Natl Acad Sci U S A. Oct. 4, 2005;102(40):14284-9. Epub Sep. 16, 2005.
Yao, et al., Fluorescent Nanoparticles Comprising Amphiphilic Rod-Coil Graft Copolymers, Macromolecules, 2008, 41:1438-43.
Ye, et al. A compact and highly fluorescent orange-emitting polymer dot for specific subcellular imaging. Chem Commun (Camb). Feb. 7, 2012;48(12):1778-80. doi: 10.1039/c2cc16486h. Epub Jan. 4, 2012.
Ye, et al. Ratiometric temperature sensing with semiconducting polymer dots. J Am Chem Soc. Jun. 1, 2011;133(21):8146-9. doi: 10.1021/ja202945g. Epub May 11, 2011.
Yu, et al. Nanoscale 3D tracking with conjugated polymer nanoparticles. J Am Chem Soc. Dec. 30, 2009;131(51):18410-4. doi: 10.1021/ja907228q.
Yu, et al. Stable functionalization of small semiconducting polymer dots via covalent cross-linking and their application for specific cellular imaging. Adv Mater. Jul. 10, 2012;24(26):3498-504. doi: 10.1002/adma.201201245. Epub Jun. 11, 2012.
Zhang, et al. Importance of having low-density functional groups for generating high-performance semiconducting polymer dots. ACS Nano. Jun. 26, 2012;6(6):5429-39. doi: 10.1021/nn301308w. Epub May 24, 2012.
Zheng. Detection of the cancer marker CD146 expression in melanoma cells with semiconductor quantum dot label (Abstract). J Biomed Nanotechnol. Aug. 2010;6(4):303-11.
"AU 2017200592 Office Action dated Mar. 29, 2018".
Australian Examination Report dated Oct. 25, 2018 for AU Application No. AU2017200592.
Co-pending U.S. Appl. No. 16/209,729, filed Dec. 4, 2018.
European search report with written opinion dated Oct. 24, 2018 for EP Application No. 18193806.
Green, et al. Simple conjugated polymer nanoparticles as biological labels. Proc. R. Soc. A. 2009. 465. 2751-2759; DOI: 10.1098/rspa.2009.0181. Published Jul. 27, 2009.
JP 2016-235598 Office Action dated Oct. 3, 2018 (w/ English translation).
Notice of allowance dated Dec. 26, 2018 for U.S. Appl. No. 13/508,981.
Office action dated Nov. 6, 2018 for EP Application No. 14770843.
Abdelwahed, et al. Freeze-drying of nanoparticles: formulation, process and storage considerations. Adv Drug Deliv Rev. Dec. 30, 2006;58(15):1688-713.
Australian examination report dated Apr. 8, 2016 for AU Application 2015204342.
Benstead, et al. Addressing fluorescence and liquid crystal behaviour in multi-mesogenic BODIPY materials. New Journal of Chemistry. 2011; 35(7):1410-1417.
Boyere, et al. Elaboration of drug nanocarriers based on a glucosamine labeled amphiphilic polymer. Polymer Chemistry. 2014; 5:3030-3037.
CN201080060982.3 Office Action dated Dec. 1, 2014.

CN201080060982.3 Office Action dated Jan. 14, 2014.
CN201080060982.3 Office Action dated Jan. 5, 2016.
CN201080060982.3 Office Action dated Jul. 31, 2015.
European office action dated Mar. 2, 2016 for EP Application No. 11835019.8.
European search report and opinion dated May 31, 2016 for EP Application No. 12861954.
European search report and opinion dated Sep. 8, 2016 for EP Application No. 14770843.2.
"Greenham, et al., Measurement of Absolute Photoluminescence Quantum Efficiencies in Conjugated Polymers, Chemical Physics Letters, Jul. 14, 1995, 241(1995) 89-96".
Japanese office action dated Jan. 8, 2019 for JP Application No. 2017092547.
"Murcia, et al., Biofunctionalization of Fluorescent Nanoparticles, Nanotechnologies for the Life Sciences, 2005, vol. 1, 40 pages.".
Nagai, et al. Highly luminescent BODIPY-based organoboron polymer exhibiting supramolecular self-assemble structure. J Am Chem Soc. Nov. 19, 2008;130(46):15276-8. doi: 10.1021/ja806939w.
Nagai, et al. Organoboron conjugated polymers. In Conjugated Polymer Synthesis: Methods and reactions. Ed. Yoshiki Chujo. Wiley-VCH Verlag GmbH & Co KGaA, Weinheim. 2010. 195-214.
"Notice of allowance dated Jun. 16, 2017 for U.S. Appl. No. 13/687,813".
"Notice of allowance dated Jun. 23, 2017 for U.S. Appl. No. 13/865,942".
"Notice of allowance dated Aug. 29, 2017 for U.S. Appl. No. 13/508,981".
Office action dated Jan. 29, 2016 for AU Application 2012362466.
Office action dated Feb. 11, 2016 for U.S. Appl. No. 13/865,942.
Office action dated Feb. 19, 2016 for CN Application 201280070923.3.
Office action dated Mar. 1, 2019 for U.S. Appl. No. 14/774,971.
"Office action dated Mar. 15, 2017 for JP Application No. 2013-535014.".
"Office action dated Apr. 28, 2017 for U.S. Appl. No. 13/865,942".
"Office action dated May 29, 2017 for CA Application No. 2,814,790.".
"Office action dated Jun. 6, 2017 for JP Application No. 2016-151438".
"Office action dated Jun. 15, 2017 for CN Application No. 201180060824.2".
"Office action dated Jul. 28, 2017 for EP Application No. 14770843".
"Office action dated Sep. 26, 2016 for CN Application No. 201480028351.1".
"Office action dated Sep. 27, 2016 for EP Application No. 11835019.8.".
Office action dated Sep. 27, 2016 for JP Application 2014-550455.
"Office action dated Nov. 4, 2016 for CN Application No. 201280070923.3.".
Riddle, et al. Signal-Amplifying Resonance Energy Transfer: A Dynamic Multichromophore Array for Allosteric Switching. Angewandte Chemie International Edition. 2007; 46(37):7019-7022.
Rong, et al. Multicolor fluorescent semiconducting polymer dots with narrow emissions and high brightness. ACS Nano. 2013; 7(1)L376-384.
CN201610969596.5 Office Action dated Aug. 23, 2018.
Sun, et al. Lyophilization of semiconducting polymer dot bioconjugates. Anal Chem. May 7, 2013;85(9):4316-20. doi: 10.1021/ac4007123. Epub Apr. 19, 2013.
"Zhang, et al., Synthesis and characterization of a novel water-soluble block copolymer with a rod-coil structure, Materials Letters 60, (2006), pp. 679-84".
Zhu, et al. Efficient tuning nonlinear optical properties: Synthesis and characterization of a series of novel poly (aryleneethynylene) s co-containing BODIPY. Journal of Polymer Science Part A: Polymer Chemistry. 2008; 46(22):7401-7410.
Communication Pursuant to Article 94(3) EPC, dated Jun. 25, 2020, for European Patent Application No. 13743132.6. (4 pages).

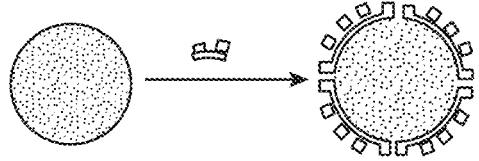
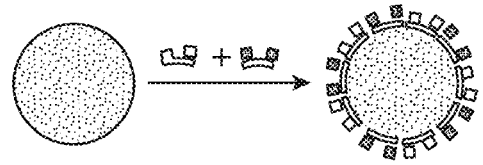
FIG. 1A FIG. 1B
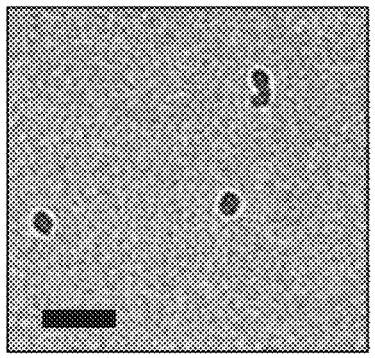
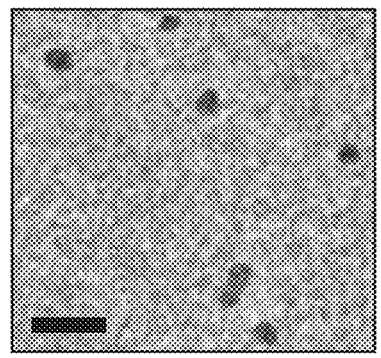
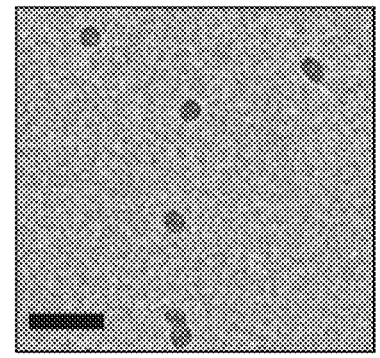
FIG. 1C FIG. 1D FIG. 1E
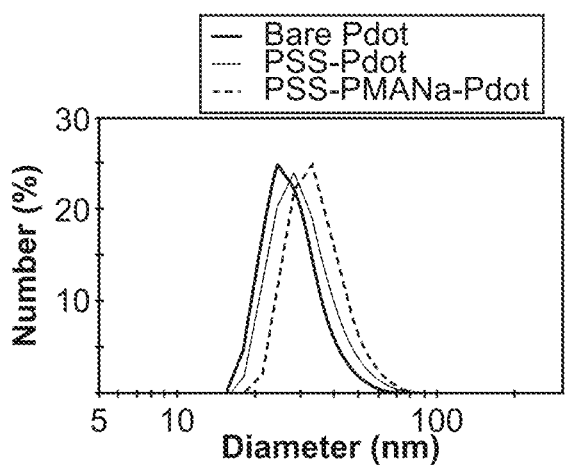
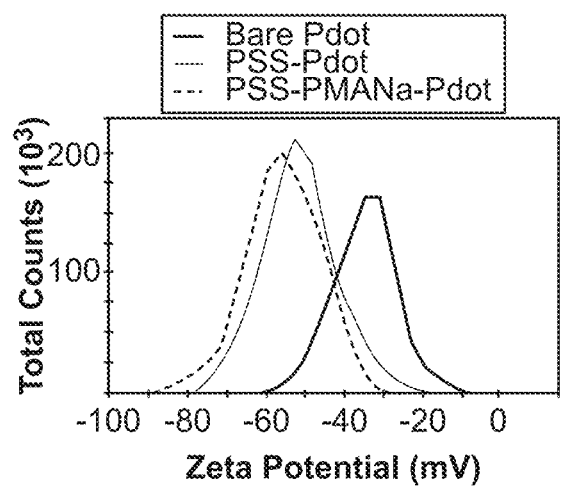
FIG. 1F FIG. 1G

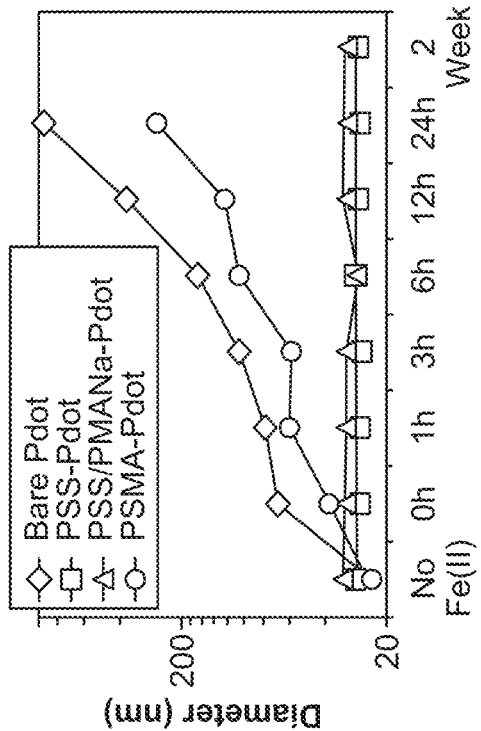
FIG. 2A
FIG. 2B
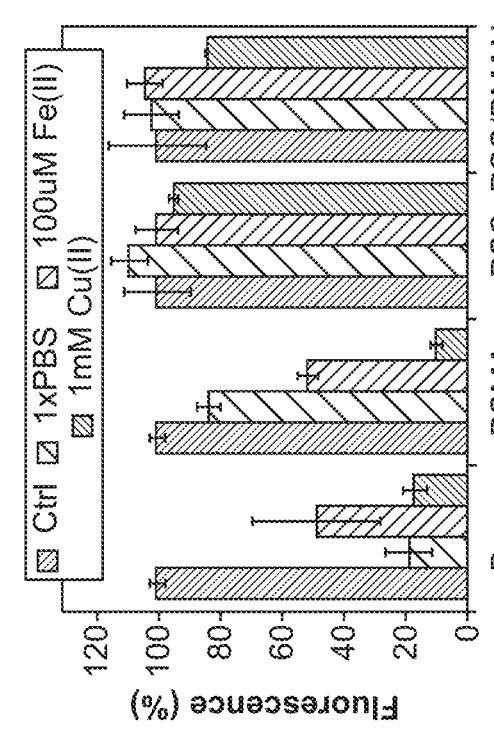
FIG. 2C
FIG. 2D

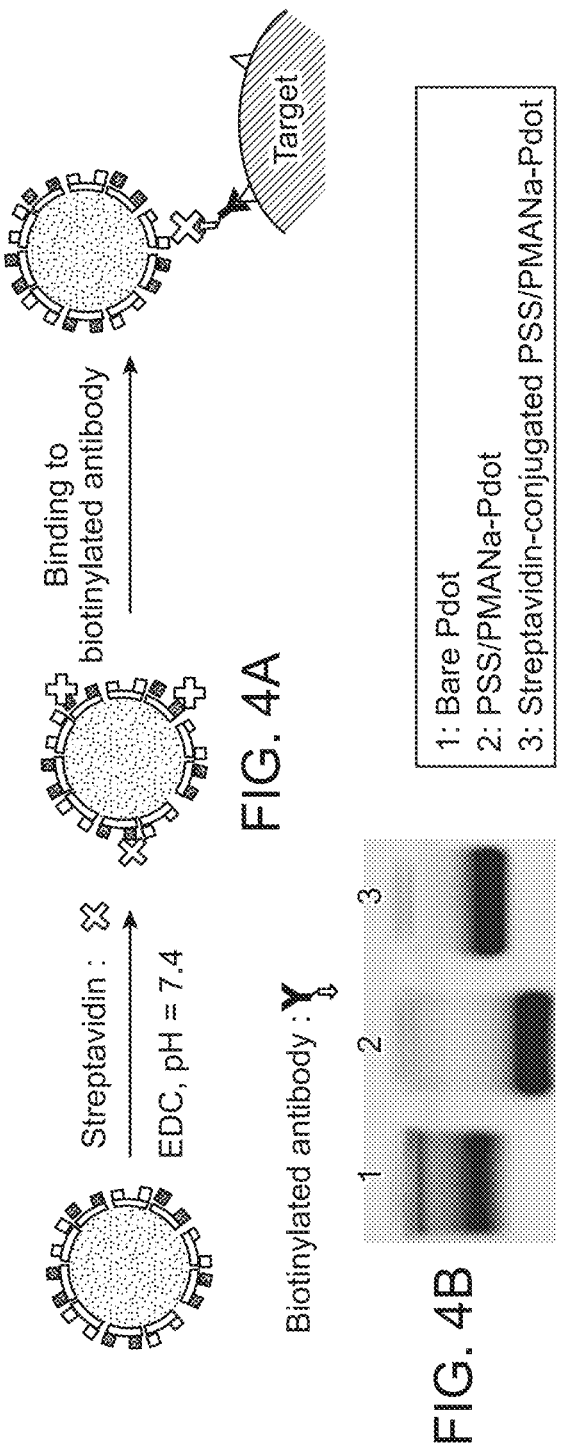
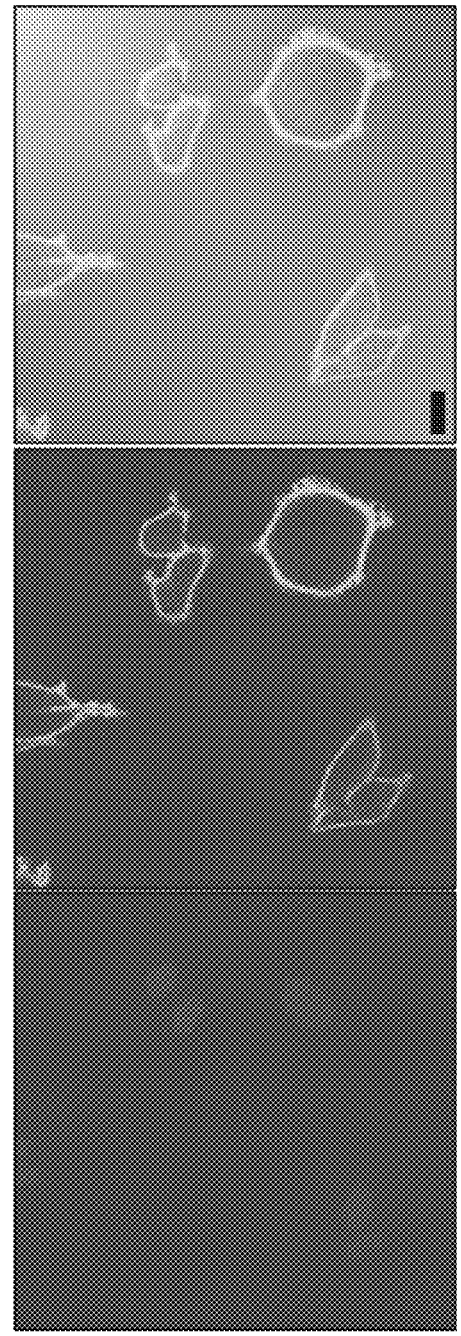
FIG. 4A
FIG. 4B
FIG. 4C
FIG. 4D
FIG. 4E

POLYELECTROLYTE-COATED POLYMER DOTS AND RELATED METHODS

CROSS-REFERENCE

This application is a continuation of U.S. patent application Ser. No. 14/373,835, filed Jul. 22, 2014, now U.S. patent Ser. No. 10/067,139, issued Sep. 4, 2018, which is a U.S. National Phase application under 35 U.S.C. § 371 of International Application No. PCT/US2013/024300, filed Feb. 1, 2013, which claims the benefit of U.S. Provisional Application No. 61/594,564, filed Feb. 3, 2012, which are incorporated herein by reference in their entireties.

STATEMENT AS TO FEDERALLY SPONSORED RESEARCH

The invention was made with government support under CA147831 and NS062725 awarded by the National Institutes of Health, and CHE-0924320 awarded by the National Science Foundation. The government has certain rights in the invention.

BACKGROUND OF THE INVENTION

Semiconducting polymer dots (Pdots) represent a new class of highly fluorescent nanoparticles with emissions tunable from the visible to the near IR region. The fluorescence intensity, e.g., of a single green-emitting Pdot can be about 30 times brighter than a single quantum dot of similar emission wavelength (Qdot565) when excited with a 488-nm laser. In addition, most Pdots exhibit excellent photostability without blinking. Previous studies have also shown that Pdots have good biocompatibility. These fluorescence properties and good biocompatibility of Pdots make them excellent probes for cellular imaging and bioassays.

Functionalizing the surface of Pdots and controlling their colloidal stability are an important consideration in translating Pdots for use in biological studies. For example, a highly charged particle can be important in many cases for colloidal stability, especially under conditions of high ionic strength, which is often encountered in biological applications. Unfortunately, many particles can aggregate over short periods of time in high ionic strength solutions due, e.g., to surface properties of the particles.

Thus, there is a need for polymer dots and compositions having improved colloidal stability in solutions, e.g., having a high ionic strength. Methods of making the polymer dots having improved colloidal stability are also desired.

SUMMARY OF THE INVENTION

The present invention provides polymer nanoparticles and related methods. For example, the present invention includes a polymer dot having a coating including a polyelectrolyte polymer. The present invention further includes methods of making and using the polymer nanoparticles disclosed herein. The polymer dots of the present invention have, e.g., can have a polyelectrolyte coating that can improve colloidal stability of the particles as compared to polymer dots not having the coating.

In some aspects, the present invention can include a nanoparticle having a condensed semiconducting polymer and a polyelectrolyte coating surrounding the condensed semiconducting polymer. In some embodiments, the polyelectrolyte coating completely surrounds the condensed semiconducting polymer. The nanoparticle can include a plurality of condensed semiconducting polymers surrounded by the polyelectrolyte coating layer. The plurality of condensed semiconducting polymers can be, e.g., physically blended or chemically crosslinked together. In some embodiments, the polyelectrolyte coating can include a polyelectrolyte selected from the group consisting of poly(styrene sulfonate), polyphosphate, polyacrylates, polymethacrylates, polyacrylate-co-maleate, polyacrylamide, chitosan, polysaccharide, polylysine, polyhistidine, and polypeptide. The polyelectrolyte coating can include a polyelectrolyte polymer in which each repeating unit of the polyelectrolyte polymer comprises a charge group selected from the group consisting of carboxyl, sulfonate, phosphate, amino, hydroxyl, and mercapto. In some aspects, the polyelectrolyte coating can include one type of polyelectrolyte. In certain aspects, the polyelectrolyte coating can include a first polyelectrolyte and a second polyelectrolyte. A first polyelectrolyte: second polyelectrolyte ratio can be, e.g., greater than about 0.1:1, greater than about 0.2:1, greater than about 0.3:1, greater than about 0.4:1, greater than about 0.5:1, greater than about 0.6:1, greater than about 0.7:1, greater than about 0.8:1, greater than about 0.9:1, or equal to about 1. In some aspects, the nanoparticles can include an anti-sticking agent, such as a polyalkylene glycol, a polysaccharide, and/or a dextran.

In another aspect, the present invention includes an aqueous composition having a population of nanoparticles. The nanoparticles can include a condensed semiconducting polymer and a polyelectrolyte coating surrounding the condensed semiconducting polymer, wherein the nanoparticles are dispersed in the aqueous composition. In some aspects, the polyelectrolyte coating modifies the zeta potential of the nanoparticle so as to exhibit improved colloidal stability as compared to the condensed polymer without the polyelectrolyte coating. The improved colloidal stability can include preventing aggregation of the nanoparticles over a period of at least one month. In certain aspects, the aqueous composition can have an ionic strength ranging between about 10 mM to about 1000 mM, between about 100 mM to about 800 mM, between about 100 mM to about 600 mM, or between about 100 mM to about 400 mM. In certain embodiments, the polyelectrolyte coating completely surrounds the condensed semiconducting polymer. At least some of the nanoparticles in the population can include a plurality of condensed semiconducting polymers surrounded by the polyelectrolyte coating layer. The plurality of condensed semiconducting polymers can be physically blended or chemically crosslinked together. In certain embodiments, the polyelectrolyte coating can include a polyelectrolyte selected from the group consisting of poly(styrene sulfonate), polyphosphate, polyacrylates, polymethacrylates, polyacrylate-co-maleate, polyacrylamide, chitosan, polysaccharide, polylysine, polyhistidine, and polypeptide. The polyelectrolyte coating can also include a polyelectrolyte polymer, wherein each repeating unit of the polyelectrolyte polymer comprises a charge group selected from the group consisting of carboxyl, sulfonate, phosphate, amino, hydroxyl, and mercapto. In certain aspects, the polyelectrolyte coating can include one type of polyelectrolyte. The polyelectrolyte coating can include a first polyelectrolyte and a second polyelectrolyte. A first polyelectrolyte: second polyelectrolyte ratio can be greater than about 0.1:1, greater than about 0.2:1, greater than about 0.3:1, greater than about 0.4:1, greater than about 0.5:1, greater than about 0.6:1, greater than about 0.7:1, greater than about 0.8:1, greater than about 0.9:1, or equal to about 1. In some aspects, at least some of the nanoparticles in the population can include an anti-sticking agent. The anti-sticking agent can include a polyalkylene glycol, a polysaccharide, and/or a dextran.

In yet another aspect, the present invention can include a method of preparing a population of nanoparticles. The methods can include, e.g., providing the population of nanoparticles having a condensed semiconducting polymer; and combining, in a first aqueous solution comprising polyelectrolytes, the population of nanoparticles having the condensed semiconducting polymer to form a population of nanoparticles having a polyelectrolyte coating surrounding the condensed semiconducting polymer of each of the nanoparticles in the population. In some aspects, the methods can also include centrifuging the first aqueous solution to separate the polyelectrolytes in the aqueous solution from the population of nanoparticles having the polyelectrolyte coating surrounding the condensed semiconducting polymer. In certain aspects, the methods can include suspending, in a second aqueous solution, the population of nanoparticles having the polyelectrolyte coating surrounding the condensed semiconducting polymer, wherein each of the nanoparticles in the population is dispersed in the second aqueous solution. In certain aspects, the methods can include a step of forming the condensed semiconducting polymer using nanoprecipitation or miniemulsion techniques. The polyelectrolyte coating can completely surround the condensed semiconducting polymer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A-1G show properties of an example functionalized Pdot with polyelectrolyte. FIG. 1A shows a schematic of coating of Pdot with a single type of polyelectrolyte (e.g. PSS). FIG. 1B depicts a coating of Pdot with multiple types of polyelectrolytes (e.g. PSS and PMANa). PSS: poly(styrene sulphonate); PMANa: poly(sodium methacrylate). FIGS. 1C-1E show TEM images of (FIG. 1C) bare Pdots, (FIG. 1D) PSS-coated Pdots, and (FIG. 1E) PSS/PMANa-coated Pdots. The scale bars represent 100 nm. The diameters and surface charges of bare Pdots, PSS-Pdots, and PSS/PMANa-Pdots were measured using DLS (FIG. 1F) and zeta potential (FIG. 1G).

FIGS. 2A-C show example changes in the size of bare Pdots, PSS-coated Pdots, and PSS/PMANa-coated Pdots in three different solutions: PBS (pH 7.4) (FIG. 2A), 1 mM Cu(II) (CuSO$_4$ in DI water) (FIG. 2C), and 100 μM Fe(II) (FeSO$_4$ in DI water) (FIG. 2B). The diameters of Pdots were monitored by DLS. Bare Pdots and Pdots formed by co-condensation with PSMA both increased in size, indicating the formation of aggregates in the three solutions; polyelectrolyte-coated Pdots showed excellent colloidal stability and no signs of aggregation. FIG. 2D shows the fluorescence intensities of bare Pdots and PSMA-blended Pdots also showed significant reduction in the three solutions, again indicating aggregation and self quenching; polyelectrolyte-coated Pdots showed excellent stability without a decrease in fluorescence emission. Control samples were dispersed in DI water.

FIGS. 4A-E shows example bioconjugation of PSS/PMANa-coated Pdots with streptavidin for labeling MCF-7 cells. FIG. 4A is a schematic showing the procedure for bioconjugation of PSS/PMANa-Pdots and their use in specific cellular targeting. FIG. 4B shows gel electrophoresis of bare Pdots, PSS/PMANa coated Pdots, and streptavidin-conjugated PSS/PMANa-Pdots. FIGS. 4C-4E show confocal fluorescence images of MCF-7 cells labeled with the streptavidin-conjugated PSS/PMANa-Pdots. FIG. 4C shows cell nuclei stained using Hoechst 34580 (blue fluorescence). FIG. 4D provides a fluorescence image of cell membrane labeled with Pdots (green fluorescence). FIG. 4E is a merged image of the labeled cells. The scale bar is 30 μm.

FIG. 6A indicates that the aggregates were observed in the solution of bare Pdots (Sample (1)). FIG. 6B indicates that the aggregates of (1) bare Pdots and (2) PSMA-Pdots were stuck on the cuvettes (green fluorescence on the walls of the top half of the cuvette). PSS-Pdots and PSS/PMANa-Pdots were free of aggregation.

DETAILED DESCRIPTION OF THE INVENTION

Figure 3A:
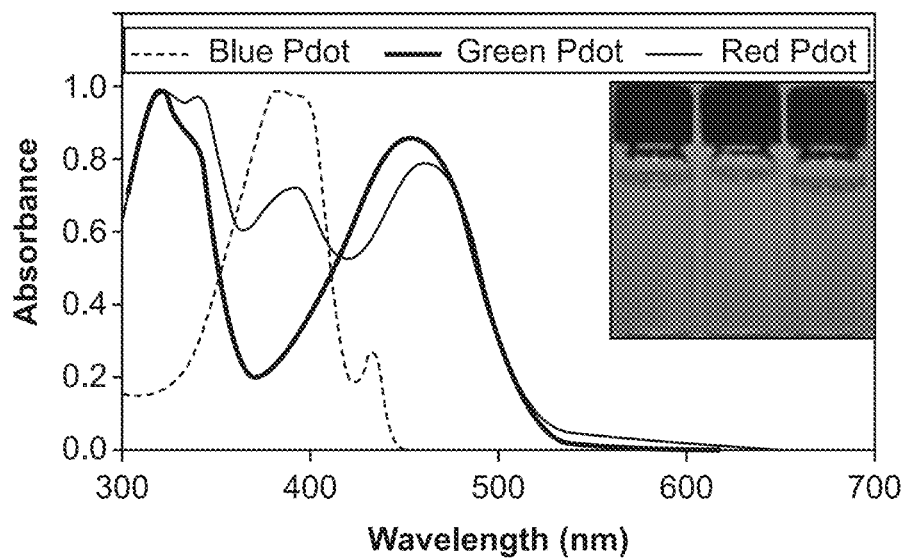
FIGS. 3A and 3B show example normalized absorption and fluorescence spectra in PBS of a blue (PFO), green (PFBT), and red (PFBT blended with PFTBT) fluorescing Pdot after coating with PSS. The inserts are optical (FIG. 3A) and fluorescence (FIG. 3B) images of the three types of PSS-coated Pdots. These spectra illustrate PSS coating can stabilize Pdots of different types.

The present invention provides polymer nanoparticles and related methods. For example, the present invention includes a polymer dot having a coating including a polyelectrolyte polymer. The present invention further includes methods of making and using the polymer nanoparticles disclosed herein.

As further described herein, the present invention provides, e.g., polymer dots and methods of making polymer dots that have a polyelectrolyte coating. Advantageously, a polyelectrolyte coating can, e.g., improve the colloidal stability of polymer dots in solutions that have high ionic strength, contain bivalent metal ions, or both. The improved colloidal stability as compared to some polymer dots without the polyelectrolyte coating, e.g., can allow polymer dots to be used under physiologically relevant environments without losing their functionality. In certain aspects, the compositional makeup of the polyelectrolyte coating can be tailored to reduce or eliminate aggregation of the polymer dots in solution, e.g., high ionic strength solutions. In addition, under certain conditions, ions (e.g., bivalent ions) in a solution can chelate groups on the surface of polymer dots, thereby affecting aggregation properties. The present invention provides further polyelectrolyte coatings that can be tailored to reduce or eliminate aggregation of the polymer dots in solution, e.g., solutions including Cu(II) and/or Fe(II). Methods of the present invention provide additional advantages, e.g., such as easy methods of making and purifying the polymer dots having a polyelectrolyte coating.

As used herein, the term "polymer dot" or "Pdot" refers to a particle structure including one or more polymers collapsed to form a stable sub-micron sized particle, e.g., a nanoparticle. In some aspects, the polymer dots are highly fluorescent nanoparticles with emissions tunable, e.g., from the visible to the near IR region. The polymer dots can include chromophoric polymers that can, e.g., absorb light and then emit light by fluorescence. In some embodiments, the polymer dots include at least one condensed polymer, e.g., a semiconducting polymer. For polymer dots having more than one condensed polymer (e.g., more than one semiconducting polymer), the condensed polymers can be the same or different types of polymers.

The polymer dots of the present invention can include a wide variety of polymers. For example, the polymer dots can include one or more conjugated polymers (e.g., semiconducting polymers). Suitable semiconducting polymers can include, but are not limited to, fluorene polymers, phenylene vinylene polymers, phenylene polymers, phenylene ethynylene polymers, benzothiazole polymers, thiophene polymers, carbazole fluorene polymers, boron-dipyrromethene-based polymers, and derivatives thereof. In some embodiments, the polymers can be homopolymers or heteropolymers including at least two different monomers (e.g., fluorene and phenylene vinylene). In certain embodiments, the polymers can be linear or branched. Other example semiconducting polymers can include poly(9,9-dihexylfluorenyl-2,7-diyl) (PDHF), poly(9,9-dioctylfluorenyl-2,7-diyl) (PFO), poly[{9,9-dioctyl-2,7-divinylene-fluorenylene}-alt-co-{2-methoxy-5-(2-ethylhexyloxy)-1,4-phenylene}] (PFPV), poly[(9,9-dioctylfluorenyl-2,7-diyl)-co-(1,4-benzo-{2,1,3}-thiadiazole)] (PFBT), or poly[(9,9-dioctylfluorenyl-2,7-diyl)-co-(4,7-di-2-thienyl-2,1,3-benzothiadiazole)] (PFTBT). Blends of polymers can also be used to make the polymer dots. For example, blends of PFBT and PFTBT can be used to further red shift the emission as compared to a PFBT polymer dot. Other suitable polymers for polymer dots can be found, e.g., in a related application PCT/US12/71767 and Conjugated Polymer Synthesis: Methods and Reactions; Editor: Yoshiki Chujo, Wiley-VCH, 2010, both of which are further incorporated by reference in their entirety.

The polymer dots can be tuned to have a wide variety of optical properties. For example, the polymer dots can have desired quantum yields, absorption properties and/or emission properties. For example, the absorption peak of the polymer dots can shift from ultra-violet region to near infrared region. In some embodiments, the absorption peak of the narrow-band emissive polymer dots can be tuned to a certain laser wavelength. In some embodiments, for example, the absorption peak can be tuned to around 266 nm. In some embodiments the absorption peak can be tuned to around 355 nm. In some embodiments, the absorption peak can be tuned to around 405 nm. In some embodiments, the absorption peak can be tuned to around 450 nm. In some embodiments, the absorption peak can be tuned to around 488 nm. In some embodiments, the absorption peak can be tuned to around 532 nm. In some embodiments, the absorption peak can be tuned to around 560 nm. In some embodiments, the absorption peak can be tuned to around 635 nm. In some embodiments, the absorption peak can be tuned to around 655 nm. In some embodiments, the absorption peak can be tuned to around 700 nm. In some embodiments, the absorption peak can be tuned to around 750 nm. In some embodiments, the absorption peak can be tuned to around 800 nm. In some embodiments, the absorption peak can be tuned to around 900 nm. In some embodiments, the absorption peak can be tuned to around 1064 nm.

The fluorescence quantum yield of the polymer dots, for example, can vary from 100% to 0.1%. In some embodiments, the quantum yield can be greater than about 90%. In some embodiments, the quantum yield can be greater than about 80%. In some embodiments, the quantum yield can be greater than about 70%. In some embodiments, the quantum yield can be greater than about 60%. In some embodiments, the quantum yield can be greater than about 50%. In some embodiments, the quantum yield can be greater than about 40%. In some embodiments, the quantum yield can be greater than about 30%. In some embodiments, the quantum yield can be greater than about 20%. In some embodiments, the quantum yield can be greater than about 10%. In some embodiments, the quantum yield can be greater than about 5%. In some embodiments, the quantum yield can be greater than about 1%.

In certain aspects, the polymers used for the polymer dots can be hydrophobic in nature and can cause the polymer dots to aggregate when added to solutions, e.g., high ionic solutions. The polymer dots can be coated (e.g., fully or partially) to modify the surface properties of the polymer dots and improve solubility in the solutions. In some aspects, the present invention includes a nanoparticle including at least one condensed semiconducting polymer and a polyelectrolyte coating (e.g., fully or partially) surrounding the condensed semiconducting polymer. As described above, the condensed semiconducting polymer(s) can form the polymer dot. The coatings of the present invention can include at least one polymer that interacts with the surface of the polymer dot and, e.g., modifies the surface properties of the polymer dot. As described further herein, the polyelectrolyte coating can be used to modify the polymer dot to reduce aggregation of the polymer dots in solution (e.g., high ionic strength solutions). The polymer dot (e.g., a condensed polymer) can be completely coated with polyelectrolyte polymers such that the coating on the nanoparticle fully shields the polymer dot from solution. This shielding can generate a surface charge on the nanoparticle that prevents aggregation of the polymer dots coating with polyelectrolyte. Advantageously, the polyelectrolyte coating does not adversely affect the optical properties of the polymer dot. While some changes may occur, the overall modifications of the optical properties still render the polymer dots useful for a wide variety of applications. The polyelectrolyte coating also does not adversely affect the size of the polymer dots. Polymer dots can be formed having a range of diameters. For example, the polymer dots can have diameters from about 10 nm to about 40 nm, from about 20 nanometer (nm) to about 35 nm, or from about 25 nm to about 35 nm. The polyelectrolyte coatings can have a layer thickness ranging from about two to four nanometers, thereby adding about four to eight nanometers to the diameter of the nanoparticle including the polymer dot and the polyelectrolyte coating.

The polyelectrolytes in the coating can form on the surface of the polymer dots in a variety of ways. For example, if one type of polyelectrolyte is used, the polyelectrolyte polymer molecules can physically blend together to form the coating. If two or more types of polyelectrolytes are used, the polyelectrolyte polymer molecules can physically blend together to form the coating or, in some embodiments, the different polyelectrolytes may form regions (or rafts) on the surface of the nanoparticle. In some embodiments, the polyelectrolytes can be chemically crosslinked. For example, the some or all of the polyelectrolytes in the coating can be chemically crosslinked using any crosslinking reaction generally well known in the art. The polyelectrolytes may also be chemically crosslinked with the condensed polymer(s) forming the polymer dot. In some aspects, the coating can include more than one layer of polyelectrolytes. For example, the coating can include two layers of polyelectrolytes, three layers of polyelectrolytes, or more layers of polyelectrolytes. The polyelectrolytes in the layers can include the same or different types of polyelectrolytes.

Suitable polymers for coating the polymer dots can include, e.g., polyelectrolytes. As referred to herein, "polyelectrolytes" can include, e.g., polymers whose repeating units bear an electrolyte group having a charge. In some embodiments, the polyelectrolytes can include polymers in which all the repeating units along the polymer bear an electrolyte group. In certain embodiments, some of the repeating units of the polymer bear an electrolyte group. For example, polyelectrolytes of the present invention can include polymers in which at least 99%, 95%, 90%, 85%, 80%, 75%, 70%, 65%, 60%, 55%, 50%, 45%, 40%, 35%, 30%, 25%, 20%, 15%, 10%, 5%, or 1% of the repeating units in the polymer bear an electrolyte group. In some embodiments, polyelectrolytes of the present invention can include polymers in which at least 99%, 95%, 90%, 85%, or 80% of the repeating units in the polymer bear an electrolyte group. In some embodiments, the polyelectrolytes can include at least one type of electrolyte group. For example, the polyelectrolytes can include only one type of electrolyte group, or two or more types of electrolyte groups. The various electrolyte groups described herein can be included in a variety of different types of polyelectrolytes. Example polyelectrolytes in the present invention can include, but are not limited to, poly(styrene sulfonate), polyphosphate, polyacrylate, polymethacrylate, polyacrylate-co-maleate, polyacrylamide, chitosan, polysaccharide, polylysine, polyhistidine, and polypeptide. The electrolyte group described herein can be included in the polymer backbone, included in side chains attached to the polymer backbone, and/or included in a group that is attached to a side chain of a polymer.

A wide variety of electrolyte groups can be used in the present invention. Generally, any group that generates a charge under certain conditions can be used for the polyelectrolytes. For example, the electrolyte group can include an anion or a cation. In some embodiments, the electrolyte group can include one anion or one cation. Alternatively, the electrolyte group can include more than one anion and/or cation such that the electrolyte group includes an overall negative or positive charge. The charge on the electrolyte groups can be a permanent charge or a charge generated according to a specific pH of a solution (e.g., a hydrogen can dissociate to form the charged electrolyte group). In some embodiments, the electrolyte group can be a salt (e.g., neutralized with a counterion) prior to being dissolved in an aqueous solution. In some embodiments, the electrolyte groups can include, but are not limited to, a carboxyl group (e.g., —COOH), a sulfonate group (e.g., —SO$_2$OH), a phosphate group (e.g., —(O)P=O(OH)$_2$ or —(O)P=O(OR)(OH)), an amino group (e.g., —NH$_2$, —N$^+$RH$_2$, —N$^+$HR$^1$R$^2$), a hydroxyl group (e.g., —OH), and a mercapto group (e.g., —SH). In some embodiments, the charges of the electrolyte groups can be generated depending on acidic or basic solution characteristics. For example, a carboxyl group, sulfonate group, phosphate group, hydroxyl group, or mercapto group can be negatively charged, e.g., according to a pH of the solution and the pKa of the respective electrolyte group. In aqueous solutions, the electrolyte groups on polymers can dissociate to form charged groups and thereby making the polymers charged, forming the polyelectrolyte. In some embodiments, the electrolyte groups can be substituted with substituents to place a permanent charge on the electrolyte group. For example, an amino group can include a quaternary ammonium cation (e.g., —N$^+$RH$_2$ or —N$^+$HR$^1$R$^2$) that has a permanent positive charge. Substituents for the electrolyte groups can be varied, such as alkyl, aryl, CN, amino, sulfide, aldehyde, ester, ether, acid, hydroxyl or halide. Substituents can be selected from: -halogen, —OR', —OC(O)R', —NR'R", —SR', —R', —CN, —NO$_2$, —CO$_2$R', —CONR'R", —C(O)R', —O C(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, in a number ranging from zero to the total number of open valences on the aromatic ring system; and where R', R" and R'" are independently selected from hydrogen, (C$_1$-C$_8$)alkyl and heteroalkyl, or unsubstituted aryl and heteroaryl. In certain embodiments, the substituents on the electrolyte groups can provide the charge to the electrolyte.

One aspect of the present invention includes modifying the zeta potential of the polymer dots by providing a polyelectrolyte coating. This coating can be used to modify, e.g., the surface charge of the nanoparticles and prevent aggregation in solutions. Depending on the solution, the zeta potential can be tailored to prevent aggregation. In some aspects, zeta potential is a parameter to evaluate whether the particles dispersed in a solution can resist aggregation. For example, particles (e.g., polymer dots coated with polyelectrolytes) will be stable (e.g., resist aggregation) when the particles have a zeta potential more positive than +30 mV or more negative than −30 mV. Higher value zeta potentials can provide more stability against aggregation. For example, a dispersion of particles with +/−60 mV can provide excellent stability. Depending on the selected polyelectrolyte(s) described herein, the present invention includes particle dispersions (e.g., polymer dots having a polyelectrolyte coating) having zeta potentials that are more positive than about +30 mV, more positive than about +40 mV, more positive than about +50 mV, or move positive than about +60 mV. The present invention includes particle dispersions (e.g., polymer dots having a polyelectrolyte coating) having zeta potentials that are more negative than about −30 mV, more negative than about −40 mV, more negative than about −50 mV, or move negative than about −60 mV. The particles having a polymer dot with a polyelectrolyte coating can be prepared using the methods described herein for the wide variety of polyelectrolytes. The zeta potential of particle dispersions can then be determined using a variety of techniques, such as by using instruments designed to measure zeta potential, e.g., by a Malvern Zetasizer.

In certain embodiments, the present invention includes nanoparticles that include a polymer dot having a coating including more than one polyelectrolyte polymer. For example, the coatings can include two different polyelectrolytes, three different polyelectrolytes, four different polyelectrolytes, or more and at any desired ratio. For two different polyelectrolytes, the coating can include a first polyelectrolyte and a second polyelectrolyte. The first polyelectrolyte:second polyelectrolyte ratio can vary over a wide range. In some embodiments, a first polyelectrolyte:second polyelectrolyte ratio is greater than about 0.1:1, greater than about 0.2:1, greater than about 0.3:1, greater than about 0.4:1, greater than about 0.5:1, greater than about 0.6:1, greater than about 0.7:1, greater than about 0.8:1, greater than about 0.9:1, or equal to about 1. In some embodiments, the first polyelectrolyte:second polyelectrolyte ratios can be at least, e.g., about 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99. For example, for the 95:5 ratio range, the first polyelectrolyte:second polyelectrolyte ratio can range from 100:0 to 95:5, such as 99:1, 98:2, 97:3, 96:4 and 95:5. This range of ratios can be applied to the other ranges above. In some embodiments, the ratios can be defined by relative weight of the first and second polyelectrolytes. For example, the coating may include 90% of the first polyelectrolyte by weight and 10% of the second polyelectrolyte by weight. In some embodiments, the number of polyelectrolytes can be used in determining the ratio. For example, for every 90 molecules of the first polyelectrolyte there can be 10 molecules of the second polyelectrolyte. In some embodiments, the first polyelectrolyte:second polyelectrolyte ratio can range between about 100:0 to about 99:1. In some embodiments, the first polyelectrolyte:second polyelectrolyte ratio can range between about 100:0 to about 95:5. In some embodiments, the first polyelectrolyte:second polyelectrolyte ratio can range between about 100:0 to about 90:10. In some embodiments, the first polyelectrolyte:second polyelectrolyte ratio can range between about 100:0 to about 85:15. In some embodiments, the first polyelectrolyte:second polyelectrolyte ratio can range between about 100:0 to about 80:20. In some embodiments, the first polyelectrolyte:second polyelectrolyte ratio can range between about 100:0 to about 75:25. In some embodiments, the first polyelectrolyte:second polyelectrolyte ratio can range between about 100:0 to about 70:30. In some embodiments, the first polyelectrolyte:second polyelectrolyte ratio can range between about 100:0 to about 65:35. In some embodiments, the first polyelectrolyte:second polyelectrolyte ratio can range between about 100:0 to about 60:40. In some embodiments, the first polyelectrolyte:second polyelectrolyte ratio can range between about 100:0 to about 55:45. In some embodiments, the first polyelectrolyte:second polyelectrolyte ratio can range between about 100:0 to about 50:50. In some embodiments, the first polyelectrolyte:second polyelectrolyte ratio can range between about 100:0 to about 45:55. In some embodiments, the first polyelectrolyte:second polyelectrolyte ratio can range between about 100:0 to about 40:60. In some embodiments, the first polyelectrolyte:second polyelectrolyte ratio can range between about 100:0 to about 35:65. In some embodiments, the first polyelectrolyte:second polyelectrolyte ratio can range between about 100:0 to about 30:70. In some embodiments, the first polyelectrolyte:second polyelectrolyte ratio can range between about 100:0 to about 25:75. In some embodiments, the first polyelectrolyte:second polyelectrolyte ratio can range between about 100:0 to about 20:80. In some embodiments, the first polyelectrolyte:second polyelectrolyte ratio can range between about 100:0 to about 15:85. In some embodiments, the first polyelectrolyte:second polyelectrolyte ratio can range between about 100:0 to about 10:90. In some embodiments, the first polyelectrolyte:second polyelectrolyte ratio can range between about 100:0 to about 5:95. In some embodiments, the first polyelectrolyte:second polyelectrolyte ratio can range between about 100:0 to about 1:99.

In some embodiments, the ratios can be identified by the relative composition (e.g., by percentage or number) of more than one electrolyte group in the coatings. For example, the coatings can include polyelectrolytes having different electrolyte groups. The different electrolyte groups can be present in one type of polyelectrolyte (e.g., a polyelectrolyte polymer including both carboxyl and sulfonate groups). Electrolyte groups can be included in the coatings using different polyelectrolytes (e.g., a first polyelectrolyte polymer having carboxyl electrolyte groups and a second polyelectrolyte polymer having sulfonate electrolyte groups). For example, the coatings can include two different electrolyte groups, three different electrolyte groups, four different electrolyte groups, or more and at any desired ratio. For two different electrolyte groups, the coating can include a first electrolyte group and a second electrolyte group. The first electrolyte group:second electrolyte group ratio can vary over a wide range. In some embodiments, a first electrolyte group:second electrolyte group can be greater than about 0.1:1, greater than about 0.2:1, greater than about 0.3:1, greater than about 0.4:1, greater than about 0.5:1, greater than about 0.6:1, greater than about 0.7:1, greater than about 0.8:1, greater than about 0.9:1, or equal to about 1. In some embodiments, the first electrolyte group:second electrolyte group ratios can be at least, e.g., about 99:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, or 1:99. For example, for the 95:5 ratio range, the first polyelectrolyte:second polyelectrolyte ratio can range from 100:0 to 95:5, such as 99:1, 98:2, 97:3, 96:4 and 95:5. This range of ratios can be applied to the other ranges above. In some embodiments, the number of polyelectrolytes can be used in determining the ratio. For example, for every 90 first electrolyte groups there can be 10 second electrolyte groups. In some embodiments, the first electrolyte group:second electrolyte group ratio can range between about 100:0 to about 99:1. In some embodiments, the first electrolyte group:second electrolyte group ratio can range between about 100:0 to about 95:5. In some embodiments, the first electrolyte group:second electrolyte group ratio can range between about 100:0 to about 90:10. In some embodiments, the first electrolyte group:second electrolyte group ratio can range between about 100:0 to about 85:15. In some embodiments, the first electrolyte group:second electrolyte group ratio can range between about 100:0 to about 80:20. In some embodiments, the first electrolyte group:second electrolyte group ratio can range between about 100:0 to about 75:25. In some embodiments, the first electrolyte group:second electrolyte group ratio can range between about 100:0 to about 70:30. In some embodiments, the first electrolyte group:second electrolyte group ratio can range between about 100:0 to about 65:35. In some embodiments, the first electrolyte group:second electrolyte group ratio can range between about 100:0 to about 60:40. In some embodiments, the first electrolyte group:second electrolyte group ratio can range between about 100:0 to about 55:45. In some embodiments, the first electrolyte group:second electrolyte group ratio can range between about 100:0 to about 50:50. In some embodiments, the first electrolyte group:second electrolyte group ratio can range between about 100:0 to about 45:55. In some embodiments, the first electrolyte group:second electrolyte group ratio can range between about 100:0 to about 40:60. In some embodiments, the first electrolyte group:second electrolyte group ratio can range between about 100:0 to about 35:65. In some embodiments, the first electrolyte group:second electrolyte group ratio can range between about 100:0 to about 30:70. In some embodiments, the first electrolyte group:second electrolyte group ratio can range between about 100:0 to about 25:75. In some embodiments, the first electrolyte group:second electrolyte group ratio can range between about 100:0 to about 20:80. In some embodiments, the first electrolyte group:second electrolyte group ratio can range between about 100:0 to about 15:85. In some embodiments, the first electrolyte group:second electrolyte group ratio can range between about 100:0 to about 10:90. In some embodiments, the first electrolyte group:second electrolyte group ratio can range between about 100:0 to about 5:95. In some embodiments, the first electrolyte group:second electrolyte group ratio can range between about 100:0 to about 1:99.

In certain embodiments, the first polyelectrolyte: second polyelectrolyte ratios or first electrolyte group:second electrolyte group ratios can be tailored for a variety of different considerations. For example, some solutions can include ions that will chelate to certain electrolyte groups in the coatings, thereby removing charges from the electrolytes and causing aggregation of the nanoparticles including the polymer dots coated with polyelectrolytes. In some instances, metal ions, such as bivalent metal ions (e.g., Cu(II) and/or Fe(II) can be present in biological buffers and solutions. The metal ions can chelate, e.g., to carboxyl groups in a polyelectrolyte coating and cause aggregation. One approach of addressing this problem can be to add at least one other electrolyte group (e.g., by adding a second polyelectrolyte) to the coating that does not chelate and can then provide charge to the surface of the nanoparticle, thereby reducing or eliminating aggregation. For example, a polyelectrolyte having a sulfonate group can be used in combination with a polyelectrolyte having a functional group (e.g., a carboxyl group) that may chelate to metal ions and affect the charge of the particles. In one example embodiment, the present invention includes polyelectrolyte-coated polymer dots in which the coating includes a percentage of PSS (having sulfonate groups) and a percentage of PSMANa (having carboxyl groups). The ratios of PSS:PSMANa can be about 99:1, 95:5, 90:10, 85:15, 80:20, 75:25, 70:30, 65:35, 60:40, 55:45, and 50:50. These ratios, e.g., can be defined as the relative number of PSS and PSMANa molecules or, alternatively, by weight. In one aspect, the amount of PSMANa can be much smaller than the PSS in which only a few (e.g., one to five) PSMANa polymer molecules are present in the polyelectrolyte coating such that a small number of possible functional groups (e.g., carboxyl groups) can be present for conjugation to another molecule, e.g., a biomolecule.

One aspect of the present invention includes the surprising ability to modify the surface properties of polymer dots to improve colloidal stability of the polymer dots. A polyelectrolyte coating, e.g., can be used to modify the surface charge of a bare polymer dot that is more hydrophobic in aqueous solutions. In certain embodiments, the polymer dots having a polyelectrolyte coating can have increased colloidal stability as compared to bare polymer dots free of a polyelectrolyte coating. Increased colloidal stability can be characterized, e.g., by an amount of time in which aggregation of the particles is prevented from occurring. Aggregation of the polymer dots in a solution (e.g., a high-ionic strength aqueous solution) can be determined using a variety of methods generally well known in the art. For example, the diameter of the polymer dots having a polyelectrolyte coating can be monitored over time using light scattering techniques (e.g., by dynamic light scattering). As aggregation occurs, the measured diameter will increase. FIG. 2A shows an example of aggregation occurring for bare polymer dots without a polyelectrolyte. As shown, the measured diameter of the bare polymer dots increased over about three hours. In contrast, the same polymer dot having different polyelectrolyte coatings (e.g., PSS-pdot or PSS/PSMANa-pdot) did not show aggregation over a period of at least two weeks in a solution of 1× phosphate buffered saline (PBS) at an ionic strength of 150 mM. In another aspect, the aggregation of the particles can be measured and monitored using fluorescence detection. As shown, e.g., FIG. 2D the fluorescence intensity of the polymer dots can reduce due to self-quenching upon aggregation. As such, as aggregation occurs the fluorescence from the polymer dots will decrease, thereby indicating if aggregation occurs. Surprisingly, the polyelectrolyte-coated polymer dots described herein have increased resistance to aggregation and show improved colloidal stability that includes prevented aggregation of the nanoparticles (e.g., the polymer dots coated with polyelectrolytes) over a period of at least two weeks, one month, two months, three months, four months, five months, six months, and longer. In some embodiments, improved colloidal stability of the coated polymer dots described herein includes prevented aggregation of the nanoparticles (e.g., the polymer dots coated with polyelectrolytes) over a period of at least two weeks or one month.

The polymer dots having a polyelectrolyte coating show improved colloidal stability in a variety of solutions that under certain conditions show aggregation of bare polymer dots without a polyelectrolyte coating. For example, the polymer dots described herein can be coated with the variety of polyelectrolytes described herein to prevent aggregation in aqueous solutions that can initiate aggregation of bare polymer dots without the polyelectrolyte coating. In certain embodiments, the polymer dots having a polyelectrolyte coating can stay dispersed without aggregating in aqueous solutions having a wide range of ionic strengths. When the particles are dispersed in the solutions, all or a vast majority of the particles (e.g., the polymer dots having a polyelectrolyte coating) will be individual particles not bound or permanently associated with other particles in the solution (e.g., by forming aggregates). In some embodiments, the polymer dots having a polyelectrolyte coating can stay dispersed without aggregating in aqueous solutions having an ionic strength of greater than about 10 mM, greater than about 50 mM, greater than about 100 mM, greater than about 150 mM, greater than about 200 mM, greater than about 300 mM, greater than about 400 mM, greater than about 500 mM, greater than about 1 M, or greater. In some embodiments, the polymer dots having a polyelectrolyte coating can stay dispersed without aggregating in aqueous solutions having an ionic strength between about 10 mM and 500 mM, between about 50 mM and 250 mM, between about 100 mM and 200 mM, between about 10 mM and 1 M, between about 100 mM and 500 mM, between about 500 mM and 1 M. In some embodiments, the polymer dots having a polyelectrolyte coating can stay dispersed without aggregating in aqueous solutions having an ionic strength ranging between about 10 mM to about 1000 mM, between about 100 mM to about 800 mM, between about 100 mM to about 600 mM, and between about 100 mM to about 400 mM. In some embodiments, the polymer dots having a polyelectrolyte coating can stay dispersed without aggregating in aqueous solutions having an ionic strength that is similar with biological conditions (e.g., physiologically relevant conditions). The aqueous solutions can include a variety of buffers and salts that are generally well known in the art and can include, e.g., PBS, HEPES, Tris, NaCl, $MgCl_2$, and others.

In addition to providing improved colloidal stability in high ionic strength solutions, the polymer dots having a polyelectrolyte coating described herein also exhibit improved colloidal stability (e.g., prevented aggregation over time) in solutions having ions or other molecules that can chelate electrolyte groups on the polyelectrolyte coating, thereby neutralizing charge on the surface and causing aggregation of the particles. In some example embodiments, metal ions in aqueous solutions can cause aggregation of the polymer dots having a polyelectrolyte coating. Bivalent metal ions that can cause aggregation include, e.g., Cu(II) and Fe(II). The Cu(II) and Fe(II) ions can, e.g., chelate to carboxyl groups in a polyelectrolyte coating and neutralize the charge of the ionized carboxyl group. To counter this affect from the metal chelating ions, the polyelectrolyte coatings can include more than one type electrolyte group. For example, a majority of the surface charge in the coating can be generated by an electrolyte group that does not chelate to metal ions (e.g., a sulfonate group). As described herein, a variety of coatings having different electrolyte groups in the coating can be used and tailored accordingly to allow for prevention of aggregation of the particles. Owing in part to the conjugation properties of carboxyl groups (or other conjugation groups, such as amino groups), certain embodiments may include carboxyl groups at low density in the polyelectrolyte coating to facilitate conjugation of the polymer dot particles to another entity, such as a biomolecule.

In some embodiments, the polymers described herein can be functionalized with a functional group. As used herein the term "functional group" refers to any chemical unit that can be attached, such as by any stable physical or chemical association, to a polymer dot and/or a polyelectrolyte coating, thereby rendering the surface of the nanoparticles herein available for conjugation or bioconjugation. As described further herein, the polyelectrolytes can include functional groups, e.g., as an electrolyte group on the polyelectrolyte polymer molecules. In some embodiments, additional functional groups can be added as well. In certain embodiments, the functional groups can be hydrophobic functional groups. Examples of hydrophobic functional groups include but not limited to alkyne, strained alkyne, azide, diene, alkene, cyclooctyne, and phosphine groups (for click chemistry). In some embodiments, functional groups can be hydrophilic functional groups. Examples of hydrophilic functional groups include but not limited to carboxylic acid or salts thereof, amino, mercapto, azido, diazo, aldehyde, ester, hydroxyl, carbonyl, sulfate, sulfonate, phosphate, cyanate, succinimidyl ester, substituted derivatives thereof. Such functional groups can be found by one of ordinary skill in the art, for example in Bioconjugate Techniques (Academic Press, New York, 1996 or later versions) the content of which is herein incorporated by reference in its entirety for all purposes.

In some embodiments, the present invention provides a bioconjugate comprising a polymer dot having a polyelectrolyte coating as described above and at least one biomolecule. It will be appreciated by one of ordinary skill that there are myriad ways to incorporate a biomolecule with the nanoparticles (e.g., polymer dots having a polyelectrolyte coating). For example, biomolecule(s) can be attached to the polymer dot and/or the polyelectrolyte coating after formation of the particles. Alternatively, the biomolecule(s) can be attached to, e.g., the polyelectrolytes and then mixed with the polymer dots to form polymer dots having a polyelectrolyte coating and a biomolecule(s) on the surface. In some embodiments, the biomolecule(s) can be attached to the polymer dot and/or a coating either directly or indirectly by a functional group. In certain embodiments, the biomolecule(s) can attach to the surface of particles (e.g., polymer dots with a polyelectrolyte coating) such that the biomolecules attach via non-covalent interactions and partially or completely cover the surface of the nanoparticles.

The bioconjugates also include polymer dots having a polyelectrolyte coating as described above, associated with biological particle such as virus, bacteria, cells, biological or synthetic vesicles such as liposomes. The term "biomolecule" is used to describe a synthetic or naturally occurring protein, glycoprotein, peptide, amino acid, metabolite, drug, toxin, nucleic acid, nucleotide, carbohydrate, sugar, lipid, fatty acid and the like. In certain embodiments, the biomolecule can include an antibody that specifically binds to a target of interest (e.g., a cancer cell). Other biomolecules can include proteins (e.g., streptavidin) that will bind to a particular small molecule of interest (e.g., avidin). A variety of different specific binding combinations are generally well known in the art and can be applied to the particles described herein. In some embodiments, the biomolecule can be attached to the functional group via a covalent bond. For example, if the functional group of the polymer dot is a carboxyl group, a protein biomolecule can be directly attached to the polymer dot by cross-linking the carboxyl group with an amine group of the protein molecule. In some embodiments, the polymer dots having a polyelectrolyte coating can have only one biomolecule attached. In some embodiments, the polymer dots having a polyelectrolyte coating can have only two biomolecule attached. The two biomolecules can be the same or different. In some embodiments, the polymer dots having a polyelectrolyte coating can have only three or more biomolecules attached. The three or more biomolecules can be the same or different. In some embodiments, the biomolecular conjugation does not change substantively the emissive properties of the polymer dots. For example, the bioconjugation does not broaden the emission spectra, does not reduce fluorescence quantum yield, and/or does not change the photostability.

In some embodiments, the polymer dots and/or the polyelectrolyte coating can be attached (e.g., covalently or non-covalently) to an anti-sticking agent. The anti-sticking agents (e.g., polymers) of the present invention can be included in the polymer dots having the polyelectrolyte coating to modify non-specific adsorption of the polymer dots having the coating with surfaces (e.g., with cells). In some aspects, the polymer dots having a polyelectrolyte coating can non-specific adsorb to cells, thereby affecting specificity for binding. The anti-sticking agents can be included to reduce non-specific adsorption. Suitable anti-sticking agents can include polymers that are generally well known in the art to reduce non-specific adsorption, such as but not limited to polyalkylene glycols (e.g., polyethylene glycol or PEG), polysaccharides, and/or dextrans. The number and/or ratio of anti-sticking agents (e.g., PEG molecules and/or polysaccharides on the particles) can be tailored to effect the level of non-specific adsorption. For example, polymer dots with a polyelectrolyte coating and an anti-sticking agent (e.g., PEG) can be mixed with cells and the level of non-specific adsorption can be detected. If sticking is problematic, the amount or ratio of anti-sticking agent (e.g., PEG) can be modified (e.g., increased) to reduce non-specific adsorption.

The present invention further includes methods of making polymer dots having a coating of polymers (e.g., polyelectrolytes). In one aspect, the present invention includes a method of preparing a population of polymer dots having a coating of polyelectrolytes. The methods, e.g., can include providing the population of nanoparticles having a condensed semiconducting polymer. The methods can further include combining, in a first aqueous solution comprising polyelectrolytes, the population of nanoparticles having the condensed semiconducting polymer to form a population of nanoparticles having a polyelectrolyte coating surrounding the condensed semiconducting polymer of each of the nanoparticles in the population. The methods of the present invention can further include centrifuging the first aqueous solution to separate the polyelectrolytes in the aqueous solution from the population of nanoparticles having the polyelectrolyte coating surrounding the condensed semiconducting polymer.

The methods of making the nanoparticles described herein (e.g., polymer dots having a polyelectrolyte coating) provide easy and quick ways to make stable particles that are, e.g., stable in solutions. In some embodiments, bare polymer dots can be made using the methods known in the art and/or described herein. The solution of bare polymer dots can be combined (e.g., mixed) with a solution having dissolved polyelectrolytes to form the polymer dots having a coating of the polyelectrolytes. In certain embodiments, the polymer dots having the coating can be further separated from the combined solution to produce a solution having purified polymer dots having the coating. Separation of the coated polymer dots can be performed using a variety of techniques, such membrane filtration, dialysis, and/or centrifugation. After separation of the polymer dots having a polyelectrolyte coating, the coated polymer dots can be mixed with a solution having polyelectrolytes (e.g., that have an opposite charge of the coating) to form a multilayered polyelectrolyte coating.

In some embodiments, the polymer dots herein can be formed using nanoprecipitation. The nanoprecipitation method involves the introduction of a solution of a polymer in a good solvent into a poor solvent, where the solubility collapse the polymer into a nanoparticle form. In certain embodiments, the polymer dots herein can be prepared using the mini-emulsion method. Other methods known in the art for making polymer dots can also be used.

The present invention further includes methods of using the polymer dot particles described herein. For example, the polymer dots having a polyelectrolyte coating can be used in a variety of detection-based methodologies. In some embodiments, the present invention provides methods of fluorescence-based detection using the polymer dots as fluorescent probes and their bioconjugates for a variety of applications, including but not limited to flow cytometry, fluorescence activated sorting, immunofluorescence, immunohistochemistry, fluorescence multiplexing, single molecule imaging, single particle tracking, protein folding, protein rotational dynamics, DNA and gene analysis, protein analysis, metabolite analysis, lipid analysis, FRET based sensors, high throughput screening, cell detection, bacteria detection, virus detection, biomarker detection, cellular imaging, in vivo imaging, bioorthogonal labeling, click reactions, fluorescence-based biological assays such as immunoassays and enzyme-based assays, and a variety of fluorescence techniques in biological assays and measurements. In certain aspects, the polymer dots disclosed herein can be used for methods of detection that involve multiplexing over a variety of wavelength ranges.

In one aspect, the present invention includes methods of detecting the polymer dots having a polyelectrolyte coating. In some embodiments, the methods of detecting can include providing polymer dots having a polyelectrolyte coating, and detecting the polymer dots having the polyelectrolyte coating. For certain applications, the polymer dots having the polyelectrolyte coating can be coupled to a molecule (e.g., covalently conjugated to a biomolecule, such as an antibody). The polymer dots that are conjugated to the molecule (e.g., the biomolecule) can be mixed with other entities of interest, such as cells. According to a binding affinity between the biomolecule and the cells, for example, the polymer dots having the polyelectrolyte coating can be used to selectively detect the cells. In certain embodiments, the methods of detecting the polymer dots can include imaging the polymer dots in two and/or three dimensions to generate images of the polymer dots. Images of the polymer dots that, e.g., are bound to specific cells can be used for selective imaging of the cells either in vitro or in vivo. In certain embodiments, the present invention can include using the polymer dots for flow cytometry. For example, the polymer dots having a polyelectrolyte coating can be specifically bound (e.g., via a biomolecule) to a cell or other particle of interest that can then be detected using flow cytometry techniques.

The present invention also provides methods and compositions for administering the polymer dots having coatings described herein to a subject to facilitate diagnostic and/or therapeutic applications. In one aspect, the present invention provides a method for administering a polymer dot composition. The method can include administering a polymer dot composition described herein to a subject. A subject can include, but is not limited to, a mouse, a rat, a rabbit, a human, or other animal. In certain embodiments, the compositions can include a population of polymer dots and a pharmaceutically acceptable excipient. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

The polymer dots of the present invention can be administered as frequently as necessary, including hourly, daily, weekly or monthly. The compounds utilized in the methods of the invention can be, e.g., administered at dosages that may be varied depending upon the requirements of the subject the severity of the condition being treated and/or imaged, and/or the polymer dot being employed. For example, dosages can be empirically determined considering the type and stage of disease diagnosed in a particular subject and/or the type of imaging modality being used in conjunction with the polymer dots. The dose administered to a subject, in the context of the present invention should be sufficient to effect a beneficial diagnostic or therapeutic response in the subject. The size of the dose also can be determined by the existence, nature, and extent of any adverse side-effects that accompany the administration of a particular polymer dot in a particular subject. Determination of the proper dosage for a particular situation is within the skill of the practitioner.

The compositions described herein can be administered to the subject in a variety of ways, including parenterally, intravenously, intradermally, intramuscularly, colonically, rectally or intraperitoneally. In some embodiments, the pharmaceutical compositions can be administered parenterally, intravenously, intramuscularly or orally. The oral agents comprising a population of the polymer dots of the invention can be in any suitable form for oral administration, such as liquid, tablets, capsules, or the like. The oral formulations can be further coated or treated to prevent or reduce dissolution in stomach.

The polymer dot compositions of the present invention can be administered to a subject using any suitable methods known in the art. Suitable formulations for use in the present invention and methods of delivery are generally well known in the art. For example, a population of polymer dots described herein can be formulated as pharmaceutical compositions with a pharmaceutically acceptable diluent, carrier or excipient. A population of polymer dots of the present invention can be administered in any pharmaceutically acceptable composition.

Furthermore, a population of polymer dots can be formulated for parenteral, topical, nasal, sublingual, gavage, or local administration. For example, the pharmaceutical compositions are administered parenterally, e.g., intravenously, subcutaneously, intradermally, or intramuscularly, or intranasally. Thus, the invention provides compositions for parenteral administration that include a solution of a single or mixture of a population of polymer dots described herein, dissolved or suspended in an acceptable carrier, e.g., an aqueous carrier. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

The present invention also provides kits for administering the polymer dots to a subject for treating and/or diagnosing a disease state. Such kits typically include two or more components useful for administration. Components can include polymer dots of the present invention, reagents, containers and/or equipment.

In certain embodiments, the kits of the present invention can include packaging assemblies that can include one or more components. For example, a packaging assembly may include a container that houses at least one of the polymer dot compositions as described herein. A separate container may include other excipients or agents that can be mixed with the polymer dot compositions prior to administration to a subject. In some embodiments, a physician may select and match certain components and/or packaging assemblies depending on the particular diagnostic and/or therapeutic application.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

EXAMPLES

This example describes a method for functionalizing semiconducting polymer dots (Pdots) with polyelectrolytes. The polyelectrolyte coating dramatically improves the colloidal stability of the Pdots in solutions which are either of high ionic strength or contain bivalent metal ions. This feature, e.g., can allow Pdots to be used under physiologically relevant environments without losing their functionality. In this example, the polyelectrolyte-coated Pdots were conjugated with streptavidin to demonstrate their application in specific cell labeling.

This example approach coats the Pdots with polyelectrolytes to control their surface and bioconjugation properties. This strategy includes several advantages for Pdot functionalization. For example, the Pdot surface is completely covered by polyelectrolytes, which significantly improves the colloidal stability of Pdots in high ionic-strength solutions. Second, the polyelectrolyte coating can improve the processibility of Pdots; coated Pdots can be centrifuged and re-suspended without aggregation. Third, functional groups on polyelectrolytes are readily accessible for further bioconjugation. Overall, this polyelectrolyte coating strategy is facile and efficient for stabilizing the Pdot surface and subsequent bioconjugation.

In one example, poly(styrene sulphonate) (PSS) and poly(sodium methacrylate) (PMANa) were used for coating the Pdot surface, but a wide range of other polyelectrolytes also can be used. FIGS. 1A and B depict the strategy of functionalizing Pdot with polyelectrolytes. To ensure complete surface coverage, Pdots were incubated with an excess amount of a specific polyelectrolyte in aqueous solution followed by the removal of the free polyelectrolytes from the coated Pdots by centrifugation at 80,000 rpm (FIG. 1A). We also extended this strategy to introduce multiple types of polyelectrolytes onto the surface of Pdots (FIG. 1B), such as PSS and PMANa; PSS serves as a stabilizer to improve the colloidal stability of the Pdots while the carboxyl groups from PMANa provide reactive sites for further bioconjugation.

For many biological applications, it is beneficial to have Pdots of small sizes because they usually exhibit better colloidal stability and mass transfer properties, which are important for efficient cellular labeling and subcellular targeting. Here, a bare green-fluorescent Pdot (poly(9,9-dioctylfluorene-co-benzothiadiazole) (PFBT)) with a diameter of 24 nm (FIG. 1C, 1F) was used. After polyelectrolyte coating, the thickness of the coated layer was about 2-4 nm. The diameters of PSS-coated (PSS-Pdot) and PSS/PMANa-coated Pdots (PSS/PMANa-Pdot) were 28 nm and 32 nm, respectively (FIG. 1D, 1F). In contrast, the surface charge, as reflected in the zeta potential of the Pdots, was altered. The values went from −35 mV for bare Pdots to −52 mV for PSS-coated Pdots, and −55 mV for PSS/PMANa-coated Pdots (FIG. 1F).

Figures 6A, 6B:
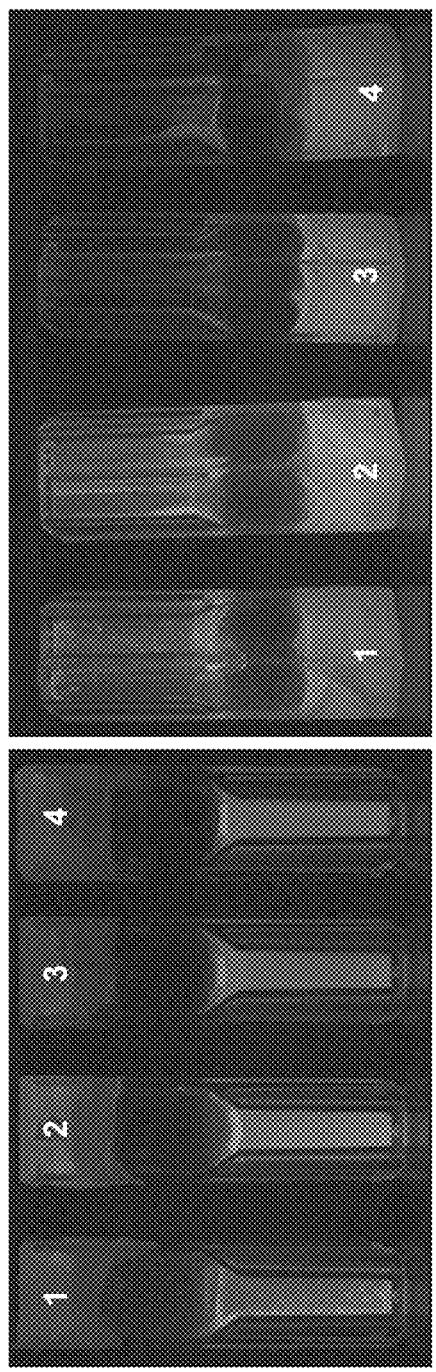
FIGS. 6A and 6B shows fluorescence Images of Pdots under UV light after the Pdots were treated with 1× PBS for 24 hours. Samples: (1) bare Pdots, (2) PSMA-Pdots, (3) PSS-Pdots, (4) PSS/PMANa-Pdots.

A key advantage of the polyelectrolyte-coated Pdots was their enhanced stability in high ionic strength solutions or in solutions that contain ions that tend to aggregate Pdots. To illustrate the improved colloidal stability bestowed by the PSS and PSS/PMANa polyelectrolyte coatings, we monitored the hydrodynamic size (FIG. 2A-2C) and fluorescence emission (FIG. 2D) from Pdots in three different solutions: Phosphate buffered saline (PBS) (FIG. 2A, 2D), 0.1 mM Fe(II) solution (FIG. 2B, 2D), and 1 mM Cu(II) solution (FIG. 2C, 2D). Both PSS-coated and PSS/PMANa-coated Pdots showed excellent colloidal stability in PBS, and their hydrodynamic diameters remained unchanged for over 2 weeks as monitored by dynamic light scattering (DLS) (FIG. 2A). In sharp contrast, bare Pdots aggregated rapidly in PBS. In fact, they completely precipitated out of solution in 6 hours (FIG. 2A). Pdots co-condensed with poly(styrene-co-maleic anhydride) (PSMA) produced PSMA-Pdots with carboxyl groups on the surface. These were prepared by nano-precipitation and displayed considerable improvement in colloidal stability in PBS. However, aggregation was still visually observed over 24 hours: the PSMA-Pdots could be seen to partially aggregate and adhere to the cuvette surface (FIG. 6)).

Measuring the intensity of fluorescence emission from Pdots is a sensitive way to monitor aggregation because even a small amount of aggregation can decrease the measured fluorescence intensity due to self quenching. FIG. 2D shows the fluorescence intensities of Pdots recorded one hour after they were dispersed in PBS, 1 mM of Cu(II), or 100 µM of Fe(II). In PBS, bare Pdots lost more than 80% of their fluorescence; PSMA-Pdots also showed a nearly 20% reduction in fluorescence intensity. Both types of polyelectrolyte-coated Pdots showed stable fluorescence without a noticeable decrease in their emission intensity.

Bivalent metal ions, such as Cu(II) and Fe(II), are often present in biological buffers and solutions in the micro- to millimolar range. Both bare Pdots and PSMA-Pdots aggregated in the solutions containing Fe(II) and Cu(II) (FIGS. 2B and 2C). For example, DLS measurements showed that the presence of 1 mM Cu(II) triggered severe and immediate aggregation of both bare and PSMA-Pdots (0 hour result, FIG. 2C). However, the mechanisms of Cu(II) and Fe(II)-induced aggregation of bare Pdots and PSMA-Pdots are different. Bare Pdots precipitated in the presence of ions because of the increase in ionic strength, which destabilized the bare Pdots. PSMA-Pdots aggregated because of specific interactions between the carboxyl groups on the PSMA-Pdot surfaces and the Cu(II) and Fe(II) ions. Neither PSS-coated nor the PSS/PMANa-coated Pdots showed signs of aggregation in Cu(II) and Fe(II) solutions (FIGS. 2B-2C) because of the improved colloidal stability of the highly negatively charged sulphonate surface. The measured fluorescence intensity from these Pdots (FIG. 2D) confirmed the DLS measurements.

In the case of PSS/PMANa-coated Pdots, PMANa does contain a large number of carboxyl groups, which can interact with Cu(II) and Fe(II) in a similar way as seen with PSMA-Pdots. However, when the Pdots were coated with both PSS (60% sulphonate group) and PMANa (40% carboxyl group), the sulphonate groups stabilized the Pdots and prevented aggregation of Pdots in the presence of Cu(II) and Fe(II) while presenting carboxyl groups for bioconjugation.

Figure 3B:
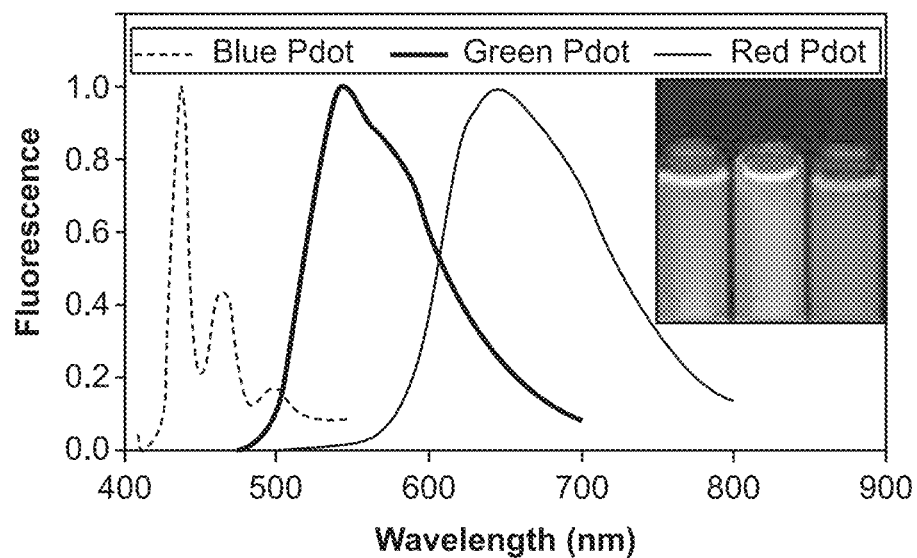
Figure 5:
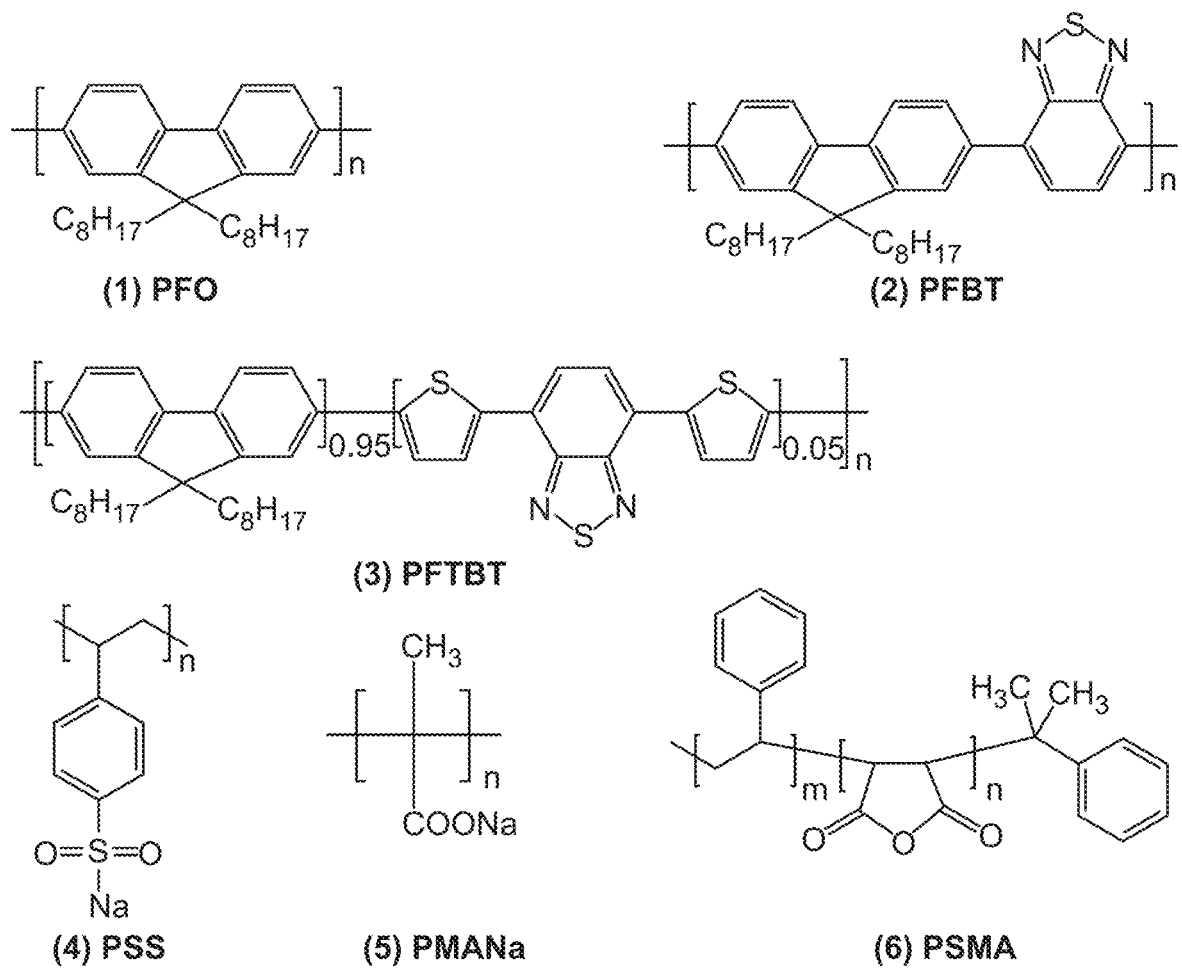
FIG. 5 shows example chemical structures of the polymers used in this study. Semiconducting Polymers: (1) PFO (blue fluorescence); (2) PFBT (green fluorescence); (3) PFTBT (red fluorescence). Polyelectrolytes: (4) PSS; (5) PMANa. Amphiphilic polymer: (6) PSMA.

To demonstrate that this polyelectrolyte coating strategy is a general method for Pdot functionalization, three types of Pdots were coated. The first two were a blue (PFO, which is (Poly(9,9-dioctylfluorenyl-2,7-diyl)) and a green (PFBT) Pdot that each consisted of one type of semiconducting polymer. The third type of Pdot was a red Pdot formed from a blend of two semiconducting polymers (PFBT and PFTBT, which is Poly(9,9-dioctylfluorene)-co-(4,7-di-2-thienyl-2,1,3-benzothiadiazole)). FIG. 3 shows the absorbance and fluorescence spectra of these three types of Pdots coated with PSS and dispersed in PBS.

To further demonstrate the applicability of polyelectrolyte-functionalized Pdots in biological applications, streptavidin was conjugated to PSS/PMANa-Pdots through EDC reaction. (FIG. 4A). Gel electrophoresis was used to verify successful streptavidin conjugation (FIG. 4B). PSS/PMANa-Pdots migrated faster than bare Pdots because of the increased surface charge. After conjugation to streptavidin, the resultant Pdots travelled much slower because of the slight increase in particle size and decrease in surface charge. Streptavidin-conjugated PSS/PMANa-Pdots was used for labeling MCF-7 cells, which is a breast cancer cell line that expresses the cell surface antigen EpCAM. We first labeled EpCAM with biotinylated primary antibody and then tagged the biotinylated primary antibodies with streptavidin functionalized Pdots (FIG. 4C-4E). This experiment demonstrates the utility of polyelectrolyte-coated Pdots for cellular targeting.

This example shows a facile and effective strategy for functionalizing Pdots using polyelectrolytes. Compared with bare Pdots or those functionalized via co-precipitation with an amphiphilic polymer (e.g. PSMA), Pdots made by this method exhibited dramatically improved colloidal stability in high ionic strength solutions, such as PBS. Moreover, multiple types of functional groups could be simultaneously introduced onto the Pdot surface by co-coating with different types of polyelectrolytes (e.g. PSS and PMANa). We showed this polyelectrolyte functionalization strategy is general enough to be applied to different types of Pdots. These Pdots can then be conjugated to biologically relevant molecules for cellular targeting. This approach will be useful, e.g., in preparing robust Pdots for demanding applications that involve harsh conditions, and where enhanced colloidal stability is required.

Materials and Methods

Materials. Polymers: Poly(9,9-dioctylfluorene)-co-(4,7-di-2-thienyl-2,1,3-benzothiadiazole) (PFTBT, red fluorescent polymer) was synthesized in our lab based on the previous reports.[1,2] Poly(9,9-dioctylfluorenyl-2,7-diyl) (PFO, blue fluorescent polymer) and poly[(9,9-dioctylfluorenyl-2,7-diyl)-co-(1,4-benzo-(2,1',3)-thiadiazole)] (PFBT, green fluorescent polymer, Mw, 157,000 Da; polydispersity, 3.0) were purchased from ADS Dyes Source, Inc. (Quebec, Canada). Polystyrene (PS, Mw, 3000 Da), and poly(sodium methacrylate) (PMANa, Mw, 7400 Da) were purchased from Polymer Source Inc. (Quebec, Canada). Poly(styrene sulphonate) (PSS, Mw, 70,000 Da), poly(styrene-co-maleic anhydride) (PSMA, cumene terminated, average Mn~1,700, styrene content 68%), and Poly(ethylene glycol) (PEG, Mw, 3350Da) were purchased from Sigma-Aldrich (St. Louis, Mo., U.S.A.). 10× PBS stock solution was purchased from EMD chemicals (Darmstadt, Germany). Biotin anti-human CD326(Ep-CAM) was purchased from BioLegend Inc. (San Diego, Calif., U.S.A.). Streptavidin was purchased from Invitrogen (Eugene, Oreg., U.S.A.). 1-ethyl-3-(3-dimethylaminopropyl) carbodiimide (EDC) was purchased from Thermo Fisher Scientific Inc. (Rockford, Ill., U.S.A.). All the other chemicals were purchased from Sigma-Aldrich (St. Louis, Mo., U.S.A.).

Bare Pdot Preparation. Pdots of blue, green, and red fluorescence were prepared using the nanoprecipitation method. In a typical preparation, the semiconducting polymer (or the mixture of polymers) was first dissolved in anhydrous tetrahydrofuran (THF) at the concentration of 0.01% (w/v). A 1-mL aliquot of the polymer solution was then quickly injected into 10 mL of DI water under vigorous sonication for 1 minute. THF was evaporated from the Pdot suspension with nitrogen purging at 80° C. The Pdot solution went through a 200-nm filter and the concentration was adjusted to 10 ppm. The green fluorescent Pdots were prepared using the THF solution that only contained PFBT. The blue fluorescent Pdots were made using a THF solution with a mixture of PFO and PS (4:6 by weight). Red fluorescent Pdots were made using a THF solution that had a mixture of PFBT and PFTBT (7:3 by weight).

PSMA-Pdot Preparation. The carboxyl-functionalized Pdots were made using the co-precipitation method that we described previously. Briefly, 250 µg of semiconducting polymer and 50 µg of amphiphilic polymer, PSMA, were mixed together in 5 mL of THF. The mixture was quickly dispensed into 10 mL of DI water under vigorous sonication.

After removing THF, the Pdot solution was filtrated and the concentration was adjusted to 50 ppm.

Determination of Pdot Concentration. A calibration curve was built up using the maximum peak absorbance (380 nm for PFO, 450 nm for PFBT and PFBT-PFTBT) from Pdot solutions that contained a series of known mass concentrations (from 1 ppm to 100 ppm). The as-prepared Pdots' mass concentration was then determined by the absorbance. We converted the mass concentration (ppm) to molar concentration by taking account of the particle size and density.

Pdot Functionalization Using Polyelectrolyte. A 4-mL aliquot of a 10 ppm solution of bare Pdots was mixed with 20 µL of 10% (w/v) negatively charged polyelectrolyte(s), such as PSS for preparing PSS-Pdot or a mixture of polyelectrolytes composed of PSS and PMANa for preparing PSS/PMANa-Pdot. Sodium chloride was then added to the mixture (final concentration is 10 mM). The mixture was slowly stirred in the dark for 1 hour. The polyelectrolyte-functionalized Pdots were collected by centrifuging the Pdots at 80,000 rpm for 1 hour using a Beckman Optima™ Max-E Ultracentrifuge.

Conjugating Streptavidin to PSS/PMANa-Pdots. A 1-mL aliquot of a 10 ppm solution of PSS/PMANa-Pdots was mixed with 80 µL of 1 mg/mL streptavidin in the reaction buffer containing 20 mM HEPES (pH=7.4) and 0.1% (w/v) PEG. After the addition of 20 µL of 5 mg/mL EDC to the mixture, the solution was gently stirred for 4 hours in the dark. It should be noted that excess amounts of streptavidin (typically, the feeding ratio of the number of streptavidin to the number of carboxyl groups from PMANa on Pdot is 20:1) was used to ensure the Pdot surface was fully covered with streptavidin. Finally, the unreacted streptavidin was removed through the Sephacryl 300HR column that was pre-flushed with a solution of 20 mM HEPES and 0.1% PEG.

Pdot Characterization. The size of Pdots was determined using a dynamic light scattering (DLS) instrument (Malvern Zetasizer Nano ZS), and a FEI Tecnai F20 transmitting electron microscope (TEM) at 200kV. The fluorescence spectra were measured using a HORIBA Jobin Yvon fluorospectrometer. The UV-Vis absorption spectra of Pdots were recorded with a DU 720 spectrophotometer. The zeta potential of the Pdots was studied by Malvern Zetasizer and gel electrophoresis experiment. The gel was prepared using 0.7% of normal melting agarose, 0.2% of PEG (MW 3350), and 20mM HEPES buffer. The Pdot samples were loaded into the electrophoresis channels with the aid of 30% glycerol and ran in 20 mM HEPES buffer (pH 7.4) under an applied field strength of 10 V/cm for 10 min using a Mupid®-exU submarine electrophoresis system. The gel was then developed using a Kodak image station 440CF system.

Evaluating Pdot Stability. The colloidal stabilities of bare Pdots, PSMA-Pdots, PSS-Pdots and PSS/PMANa-Pdots were investigated and compared at the same concentration in phosphate buffered saline (1× PBS), 1 mM of $Cu^{2+}$ ion ($CuSO_4$), and 100 µM of $Fe^{2-}$ ion ($FeSO_4$). The size of the Pdots was periodically tracked after the addition of PBS or metal ions using DLS. The fluorescence intensities of Pdots were also compared before and after the addition of saline and metal ion solutions.

Cell culture. The breast cancer cell line MCF-7 was ordered from American Type Culture Collection (ATCC, Manassas, Va., U.S.A.). Cells were cultured at 37° C. with 5% $CO_2$ in Eagle's minimum essential medium (EMEM) supplemented with 10% Fetal Bovine Serum (FBS), 50 U/mL penicillin, and 50 µg/mL streptomycin. Ten thousands of MCF-7 cells were plated on a 15-mm-diameter glass-bottomed culture dish and cultured until the density reached confluence for Pdot labelling and fluorescence imaging.

Labeling Cells Using Streptavidin-Functionalized Pdots. For labeling cell-surface markers with PSS/PMANa-Pdot-streptavidin conjugates, live MCF-7 cells in the glass-bottomed culture dish were incubated first with 5 µg/mL biotin anti-human CD326 antibody and then with 5 nM PSS/PMANa-Pdot-streptavidin. Each incubation lasted for 1 hour followed by two washing steps. The confocal fluorescence image of the Pdot-labeled MCF-7 cells was then acquired using a fluorescence confocal microscope (Zeiss LSM 510).

TABLE 1

Quantum yield of bare and polyelectrolyte coated Pdots

| | Bare | PSS coated | PSS/PMANa coated |
|---|---|---|---|
| PFO | 40% | 38% | 37% |
| PFBT | 32% | 32% | 34% |
| PFBT-PFTBT | 56% | 50% | 52% |

What is claimed is:

1. A nanoparticle comprising:
   a polymer dot comprising a condensed semiconducting polymer; and
   a polyelectrolyte coating that surrounds the condensed semiconducting polymer, the polyelectrolyte coating comprising a first polyelectrolyte polymer and a second polyelectrolyte polymer, wherein the first polyelectrolyte polymer is poly(styrene sulfonate) and the second polyelectrolyte polymer is poly(sodium methacrylate).

2. The nanoparticle of claim 1, wherein the nanoparticle has a zeta potential more positive than +50 mV or more negative than −50 mV.

3. The nanoparticle of claim 1, comprising a plurality of condensed semiconducting polymers surrounded by the polyelectrolyte coating layer.

4. The nanoparticle of claim 3, wherein the plurality of condensed semiconducting polymers is physically blended or chemically crosslinked together.

5. The nanoparticle of claim 1, wherein the condensed semiconducting polymer is fluorescent.

6. The nanoparticle of claim 1, wherein a mass:mass ratio of the first polyelectrolyte polymer to the second polyelectrolyte polymer is greater than about 0.9:1.

7. The nanoparticle of claim 1, further comprising an anti-sticking agent.

8. The nanoparticle of claim 7, wherein the anti-sticking agent is selected from the group consisting of a polyalkylene glycol, a polysaccharide, and a dextran.

9. The nanoparticle of claim 1, wherein at least 80% of repeating units of the first polyelectrolyte polymer or the second polyelectrolyte polymer comprise an electrolyte group.

10. The nanoparticle of claim 1, wherein the polyelectrolyte coating comprises at least one site capable of bioconjugation.

11. The nanoparticle of claim 10, wherein the nanoparticle is conjugated to a biomolecule.

12. The nanoparticle of claim 11, wherein the biomolecule comprises a protein, a peptide, an amino acid, a nucleic acid, a nucleotide, a carbohydrate, a lipid, a fatty acid, or a combination thereof.

13. The nanoparticle of claim 11, wherein the biomolecule comprises an antibody, a glycoprotein, a metabolite, a drug, a toxin, a sugar, a streptavidin, or a combination thereof.

14. The nanoparticle of claim 1, wherein the nanoparticle has a diameter from about 10 nm to about 40 nm.

15. A plurality of nanoparticles comprising:
a nanoparticle comprising:
a polymer dot comprising a condensed semiconducting polymer dispersible in an aqueous solution; and
a polyelectrolyte coating that surrounds the condensed semiconducting polymer, the polyelectrolyte coating comprising a first polyelectrolyte polymer and a second polyelectrolyte polymer, wherein the first polyelectrolyte polymer is poly(styrene sulfonate) and the second polyelectrolyte polymer is poly(sodium methacrylate).

16. The plurality of nanoparticles of claim 15, wherein a majority of the plurality of nanoparticles do not aggregate, as measured by suspension in PBS for 1 month.

17. The nanoparticle of claim 16, wherein the nanoparticle is conjugated to a biomolecule.

18. The nanoparticle of claim 17, wherein the biomolecule comprises a protein, a peptide, an amino acid, a nucleic acid, a nucleotide, a carbohydrate, a lipid, a fatty acid, or a combination thereof.

19. A nanoparticle comprising:
a polymer dot comprising a plurality of condensed semiconducting polymers; and
a polyelectrolyte coating that surrounds the plurality of condensed semiconducting polymers, the polyelectrolyte coating comprising a first polyelectrolyte polymer and a second polyelectrolyte polymer, wherein the first polyelectrolyte polymer is poly(styrene sulfonate) and the second polyelectrolyte polymer is poly(sodium methacrylate).

20. The nanoparticle of claim 1, wherein the first polyelectrolyte polymer or second polyelectrolyte polymer comprises repeating units, and at least 25% of the repeating units bear an electrolyte group.

21. The nanoparticle of claim 1, wherein the condensed semiconducting polymer comprises a hydrophilic functional group.

* * * * *